(12) United States Patent
Alam et al.

(10) Patent No.: US 8,470,847 B2
(45) Date of Patent: Jun. 25, 2013

(54) DERIVATIVES OF 7-ALKYNYL-1,8-NAPHTHYRIDONES, PREPARATION METHOD THEREOF AND USE OF SAME IN THERAPEUTICS

(75) Inventors: Antoine Alam, Paris (FR); Sandrine Biscarrat, Paris (FR); Isabelle Blanc, Paris (FR); Françoise Bono, Paris (FR); Olivier Duclos, Paris (FR); Gary Mccort, Paris (FR)

(73) Assignee: Sanofi, Paris (FR)

( * ) Notice: Subject to any disclaimer, the term of this patent is extended or adjusted under 35 U.S.C. 154(b) by 371 days.

(21) Appl. No.: 12/631,122

(22) Filed: Dec. 4, 2009

(65) Prior Publication Data

US 2010/0144757 A1 Jun. 10, 2010

Related U.S. Application Data

(63) Continuation of application No. PCT/FR2008/000793, filed on Jun. 11, 2008.

(30) Foreign Application Priority Data

Jun. 13, 2007 (FR) ..................................... 07 04192

(51) Int. Cl.
C07D 471/02 (2006.01)
A01N 43/42 (2006.01)
A61K 31/44 (2006.01)

(52) U.S. Cl.
USPC .......................................... 514/300; 546/123

(58) Field of Classification Search
USPC ............... 514/255.05, 300; 546/123; 544/405
See application file for complete search history.

(56) References Cited

U.S. PATENT DOCUMENTS

2010/0144782 A1* 6/2010 Alam et al. .................... 514/300

FOREIGN PATENT DOCUMENTS

| EP | 0 978 516 A1 | 2/2000 |
| WO | WO 97/04775 | 2/1997 |
| WO | WO 02/094823 A1 | 11/2002 |
| WO | WO 2005/118587 A1 | 12/2005 |

OTHER PUBLICATIONS

U.S. Appl. No. 12/631,130—Non-Final Office Action Dated Sep. 29, 2011.
U.S. Appl. No. 12/631,130—Response to Non-Final Office Action dated Sep. 29, 2011, filed Jan. 30, 2012.
U.S. Appl. No. 12/631,130, Alam et al, date of publication, Dec. 4, 2009,
Ishikawa et al, Preparation of Carboxylic Acid Fluorides Using Hexafluoro-1,2-Epdxypropane, Chem. Lett., 1976 pp. 1407-1408.
Kakinuma et al, Diacetone Glucose Architecture as a Chirality Template I. Crucial Effects of the Intramolecular Oxygens upon the LiAIH4 Reduction of the Propargyl Alcohol of 3-C-Ethynyl-1,2:5,6-di-O-isopropylidene-alpha-D-allofuranose Derivatives, Tetrahedron 1991 (47) 34 pp. 6975-6982.
Mukaiyama et al, A Convenient Method for the Preparation of Carboxylic Acid Fluorides, Chem. Lett., 1976 pp. 303-306.
Olah et al, Synthetic Methods and Reactions; IV. Fluorination of Carboxylic Acids with Cyanuric Fluoride, *Synthesis*, 1973 pp. 487-488.
International Search Raport for WO2009/007535 dated Jan. 15, 2009.
Boto. et al.. Efficient and Selective Removal of Methoxy Protecting Groups in Carbohydrates, Organic Letters, (2004), vol. 6, No. 21, pp. 3785-3788.
Notice of Allowance for U.S. Appl. No. 12/631,130, dated Mar. 2, 2012.
Nagasaki, et al.. Studies on the Antibacterial Activity of 1-Substituted 1,4-Dihydro-7-[2-(5-nitro-2-furyl) vinyl]-4-oxo-1,8-naphthyridine Derivatives, Chemical & Pharmaceutical Bulletin, vol. 20, No. 4, pp. 639-649, (1972).

* cited by examiner

Primary Examiner — Niloofar Rahmani

(57) ABSTRACT

The disclosure relates to 7-alkynyl-1,8-naphthyridones of formula (I):

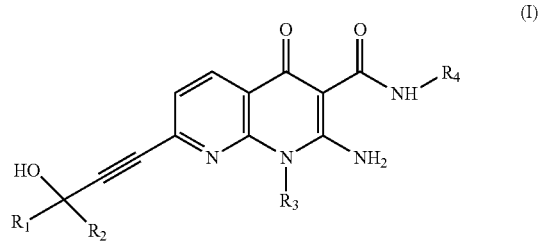

wherein $R_1$, $R_2$, $R_3$, and $R_4$ are as defined in the disclosure, to compositions containing them, to processes for preparing them, and to their use in therapeutics.

12 Claims, No Drawings

DERIVATIVES OF 7-ALKYNYL-1,8-NAPHTHYRIDONES, PREPARATION METHOD THEREOF AND USE OF SAME IN THERAPEUTICS

The present invention relates to 7-alkynyl-1,8-naphthyridone derivatives, to the preparation thereof and to the therapeutic use thereof.

A subject of the present invention is compounds corresponding to formula (I):

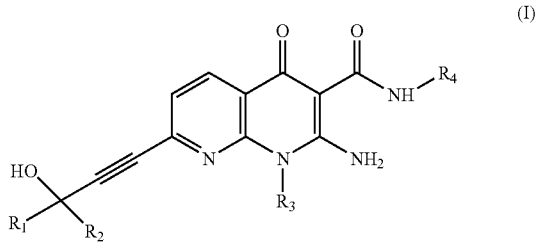

in which:
$R_1$ and $R_2$
(1) are, independently of one another:
either a hydrogen atom,
or a $C_1$-$C_7$ alkyl group, a —CO—($C_1$-$C_7$) alkyl group or a $C_3$-$C_8$ cycloalkyl group, where said alkyl and cycloalkyl groups are optionally substituted with one or more groups selected from halogen atoms and hydroxyl and alkoxy groups,
or a phenyl group optionally substituted with one or more groups selected from halogen atoms, and $C_1$-$C_4$ alkyl, $C_1$-$C_4$ alkoxy, hydroxyl, -haloalkoxy, -haloalkyl, —CN or —NRR' groups, where R and R' are as defined below,
or a heteroaryl group optionally substituted in any positions, including on a nitrogen atom of said heteroaryl, with one or more groups selected from halogen atoms, $C_1$-$C_4$ alkyl groups and —NRR' groups, where R and R' are as defined below,
(2) or $R_1$ and $R_2$ form, together with the carbon atom that bears them:
either a $C_4$-$C_8$ cycloalkyl group,
or a 4- to 8-membered saturated heterocyclic group comprising a heteroatom selected from N, O and S atoms,
and it being possible for said heterocyclic group to be fused with a phenyl group;
$R_3$ is:
either a linear or branched $C_1$-$C_7$ alkyl group or a $C_3$-$C_7$ alkyl group in which at least 3 carbon atoms are cyclized, said alkyl group being optionally substituted with one or more groups selected from halogen atoms and hydroxyl, alkoxy, —NRR', -haloalkyl and —SO$_2$—($C_1$-$C_4$)alkyl groups, where R and R' are as defined hereinafter,
or a —(CH$_2$)$_n$-heterocyclic group, where n=0, 1, 2 or 3 and where the heterocyclic group comprises between 4 and 8 members and comprises at least one heteroatom selected from N, O and S atoms, where said heterocyclic group is optionally substituted with an oxo group,
or a —(CH$_2$)$_n$-heteroaryl group, where n=0, 1, 2 or 3 and where the heteroaryl group comprises 5 or 6 members and comprises one or more heteroatoms selected from nitrogen, oxygen and sulphur;
$R_4$ is a hydrogen atom, a $C_1$-$C_4$ alkyl group or a $C_1$-$C_4$ alkoxy group;

R and R' are, independently of one another, a hydrogen atom or a $C_1$-$C_4$ alkyl group.

The compounds of formula (I) may comprise one or more asymmetrical carbon atoms.

They may therefore exist in the form of enantiomers or of diastereoisomers. These enantiomers and diastereoisomers, and also mixtures thereof, including the racemic mixture thereof, are part of the invention.

The compounds of formula (I) may exist in the form of bases or in a form salified with acids or bases, in particular pharmaceutically acceptable acids or bases. Such addition salts are part of the invention. These salts are advantageously prepared with pharmaceutically acceptable acids or bases, but the salts of other acids or bases that can be used, for example, for purifying or isolating the compounds of formula (I) are also part of the invention.

The compounds according to the invention may also exist in the form of hydrates or of solvates, i.e. in the form of associations or of combinations with one or more molecules of water or with a solvent. Such hydrates and solvates are also part of the invention.

In the context of the present invention, and unless otherwise mentioned in the text:
the term "an alkyl group" is intended to mean: a saturated aliphatic group containing from 1 to 7 carbon atoms (advantageously from 1 to 4 carbon atoms) and being linear or, when the alkyl chain contains at least 3 carbon atoms, possibly being linear, branched or partially cyclized. By way of examples, mention may be made of methyl, ethyl, propyl, isopropyl, butyl, isobutyl, tert-butyl, methylenecyclopropyl, methylenecyclohexyl, pentyl, 2,2-dimethylpropyl, hexyl, heptyl, etc, groups;
the term "a cycloalkyl group" is intended to mean: a cyclic alkyl group containing from 3 to 8 carbon atoms and in which all the carbon atoms are involved in the ring. Mention may be made of cyclopropyl, cyclobutyl, cyclopentyl, cyclohexyl and cycloheptyl groups;
the term "an alkoxy group" is intended to mean: an —O-alkyl group, where the alkyl group is as defined above;
the term "a halogen atom" is intended to mean: a fluorine, a chlorine, a bromine or an iodine;
the term "a haloalkyl group" is intended to mean: an alkyl group in which one or more hydrogen atoms has (have) been substituted with a halogen atom; by way of example, mention may be made of —CF$_3$;
the term "a haloalkoxy" is intended to mean: an alkoxy group in which one or more hydrogen atoms has (have) been substituted with a halogen atom; by way of example, mention may be made of —OCF$_3$,
the term "an aryl group" is intended to mean: a monocyclic aromatic group, such as a phenyl group;
the term "a heteroaryl group" is intended to mean: an aromatic group comprising 5 or 6 members and comprising one or more heteroatoms selected from nitrogen, oxygen and sulphur. Mention may, for example, be made of pyridinyl, furanyl, thienyl, pyrimidyl, pyrazinyl and thiazolyl groups; and
the term "a heterocyclic group" is intended to mean: a cyclic alkyl group comprising between 4 and 8 members and comprising one or more heteroatoms selected from nitrogen, oxygen and sulphur. Mention may, for example, be made of piperidinyl, pyrrolidinyl, oxetanyl, tetrahydrofuranyl, tetrahydropyranyl and tetrahydrothienyl groups.

Among the compounds of formula (I) which are subjects of the invention, mention may be made of a subgroup of compounds which is defined as follows:
$R_1$ and $R_2$ (3) are, independently of one another:
either a hydrogen atom,
or a $C_1$-$C_7$ alkyl group, a —CO—$(C_1$-$C_7)$alkyl group or a $C_3$-$C_8$ cycloalkyl group, where said alkyl and cycloalkyl groups are optionally substituted with one or more groups selected from halogen atoms and hydroxyl and alkoxy groups,
or a phenyl group optionally substituted with one or more groups selected from halogen atoms, and $C_1$-$C_4$ alkyl, $C_1$-$C_4$ alkoxy, hydroxyl, —OCF$_3$, —CF$_3$, —CN or —NRR' groups, where R and R' are as defined below,
or a heteroaryl group optionally substituted in any positions, including on a nitrogen atom of said heteroaryl, with one or more groups selected from halogen atoms, $C_1$-$C_4$ alkyl groups and —NRR' groups, where R and R' are as defined below,
(4) or $R_1$ and $R_2$ form, together with the carbon atom that bears them:
either a $C_4$-$C_8$ cycloalkyl group,
or a 4- to 8-membered saturated heterocyclic group comprising a heteroatom chosen from N, O and S atoms,
and it being possible for said heterocyclic group to be fused with a phenyl group;
$R_3$ is:
either a linear or branched $C_1$-$C_7$ alkyl group or a $C_3$-$C_7$ alkyl group in which at least 3 carbon atoms are cyclized, said alkyl group being optionally substituted with one or more groups selected from halogen atoms and hydroxyl, alkoxy, —NRR', —CF$_3$ and —SO$_2$—$(C_1$-$C_4)$alkyl groups, where R and R' are as defined hereinafter;
or a —(CH$_2)_n$-heterocyclic group, where n=0, 1, 2 or 3 and where the heterocyclic group comprises between 4 and 8 members and comprises at least one heteroatom selected from N, O and S atoms, where said heterocyclic group is optionally substituted with an oxo group,
or a —(CH$_2)_n$-heteroaryl group, where n=0, 1, 2 or 3 and where the heteroaryl group comprises 5 or 6 members and comprises one or more heteroatoms selected from nitrogen, oxygen and sulphur;
$R_4$ is a hydrogen atom, a $C_1$-$C_4$ alkyl group or a $C_1$-$C_4$ alkoxy group;
R and R' are, independently of one another, a hydrogen atom or a $C_1$-$C_4$ alkyl group.

Among the compounds of formula (I) which are subjects of the invention, mention may be made of a subgroup of compounds which is defined as follows:
$R_1$ and $R_2$
(1) are, independently of one another:
either a hydrogen atom,
or a $C_1$-$C_7$ alkyl group, a —CO—$(C_1$-$C_7)$alkyl group or a $C_3$-$C_8$ cycloalkyl group, where said alkyl group is optionally substituted with one or more groups selected from hydroxyl and alkoxy groups,
or a phenyl group optionally substituted with one or more $C_1$-$C_4$ alkoxy groups,
or a heteroaryl group,
(2) or $R_1$ and $R_2$ form, together with the carbon atom which bears them:
either a $C_4$-$C_8$ cycloalkyl group,
or a 4- to 8-membered saturated heterocyclic group comprising a heteroatom selected from N, O and S atoms,
and it being possible for said heterocyclic group to be fused with a phenyl group;
and/or
$R_3$ is:
either a linear or branched $C_1$-$C_7$ alkyl group or a $C_3$-$C_7$ alkyl group in which at least 3 carbon atoms are cyclized, said alkyl group being optionally substituted with one or more groups selected from hydroxyl, alkoxy, —NRR', haloalkyl and —SO$_2$—$(C_1$-$C_4)$alkyl groups, where R and R' are as defined hereinafter;
or a —(CH$_2)_n$-heterocyclic group, where n=0, 1, 2 or 3 and where the heterocyclic group comprises between 4 and 8 members and comprises at least one heteroatom selected from N and O atoms, where said heterocyclic group is optionally substituted with an oxo group,
or a —(CH$_2)_n$-heteroaryl group, where n=0 or 1 and where the heteroaryl group comprises 5 or 6 members and comprises one or more nitrogen heteroatoms;
and/or
$R_4$ is a $C_1$-$C_4$ alkyl group or a $C_1$-$C_4$ alkoxy group;
and/or
R and R' are each a linear or branched $C_1$-$C_4$ alkyl group.

Among the compounds of formula (I) which are subjects of the invention, mention may be made of another subgroup of compounds which is defined as follows:
$R_1$ and $R_2$
(1) are, independently of one another:
either a hydrogen atom,
or a $C_1$-$C_7$ alkyl group, a —CO—$(C_1$-$C_7)$alkyl group or a $C_3$-$C_8$ cycloalkyl group, where said alkyl group is optionally substituted with one or more groups selected from hydroxyl and alkoxy groups,
or a phenyl group optionally substituted with one or more $C_1$-$C_4$ alkoxy groups,
or a heteroaryl group,
(2) or $R_1$ and $R_2$ form, together with the carbon atom which bears them:
either a $C_4$-$C_8$ cycloalkyl group,
or a 4- to 8-membered saturated heterocyclic group comprising an oxygen heteroatom,
and it being possible for said heterocyclic group to be fused with a phenyl group;
and/or
$R_3$ is:
either a linear or branched $C_1$-$C_7$ alkyl group or a $C_3$-$C_7$ alkyl group in which at least 3 carbon atoms are cyclized, said alkyl group being optionally substituted with one or more groups selected from hydroxyl, alkoxy, —NRR', haloalkyl and —SO$_2$—$(C_1$-$C_4)$alkyl groups, where R and R' are as defined hereinafter;
or a —(CH$_2)_n$-heterocyclic group, where n=0, 1, 2 or 3 and where the heterocyclic group comprises between 4 and 8 members and comprises at least one heteroatom selected from N and O atoms, where said heterocyclic group is optionally substituted with an oxo group,
or a —(CH$_2)_n$-heteroaryl group, where n=0 or 1 and where the heteroaryl group comprises 5 or 6 members and comprises one or more nitrogen heteroatoms;
and/or
$R_4$ is a $C_1$-$C_4$ alkyl group or a $C_1$-$C_4$ alkoxy group;
and/or
R and R' are each a linear or branched $C_1$-$C_4$ alkyl group.

Among the compounds of formula (I) which are subjects of the invention, mention may be made of a third subgroup of compounds which is defined as follows:
$R_1$ and $R_2$
(1) are, independently of one another:
either a hydrogen atom,
or a $C_1$-$C_7$ alkyl group or a $C_3$-$C_8$ cycloalkyl group, where said alkyl group is optionally substituted with one or more groups selected from hydroxyl and alkoxy groups,
or a phenyl group optionally substituted with one or more $C_1$-$C_4$ alkoxy groups,
or a heteroaryl group, (2) or R₁ and R₂ form, together with the carbon atom which bears them, a $C_4$-$C_8$ cycloalkyl group;
and/or
R₃ is:
either a linear or branched $C_1$-$C_7$ alkyl group or a $C_3$-$C_7$ alkyl group in which at least 3 carbon atoms are cyclized, said alkyl group being optionally substituted with one or more groups selected from hydroxyl, alkoxy, haloalkyl and —SO₂—($C_1$-$C_4$)alkyl groups;
or a —(CH₂)$_n$-heterocyclic group, where n=0, 1, 2 or 3 and where the heterocyclic group comprises between 4 and 8 members and comprises at least one heteroatom selected from N and O atoms, where said heterocyclic group is optionally substituted with an oxo group,
or a —(CH₂)$_n$-heteroaryl group, where n=0 or 1 and where the heteroaryl group comprises 5 or 6 members and comprises one or more nitrogen heteroatoms;
and/or
R₄ is a $C_1$-$C_4$ alkyl group;
and/or
R and R' are each a linear or branched $C_1$-$C_4$ alkyl group.

Among the compounds of formula (I) which are subjects of the invention, mention may be made of a subgroup of compounds for which R₁ and R₂
(1) are, independently of one another:
either a hydrogen atom,
or a $C_1$-$C_7$ alkyl group, a —CO—($C_1$-$C_7$)alkyl group or a $C_3$-$C_8$ cycloalkyl group, where said alkyl group is optionally substituted with one or more groups selected from hydroxyl and alkoxy groups,
or a phenyl group optionally substituted with one or more $C_1$-$C_4$ alkoxy groups,
or a heteroaryl group,
(2) or R₁ and R₂ form, together with the carbon atom which bears them:
either a $C_4$-$C_8$ cycloalkyl group,
or a 4- to 8-membered saturated heterocyclic group comprising a heteroatom selected from N, O and S atoms,
and it being possible for said heterocyclic group to be fused with a phenyl group.

More particularly, among the compounds of formula (I) which are subjects of the invention, mention may be made of a subgroup of compounds for which R₁ and/or R₂ is (are) a pyridinyl, thienyl, thiazolyl, pyrazinyl or imidazolyl group.

More particularly, among the compounds of formula (I) which are subjects of the invention, mention may be made of a subgroup of compounds for which R₁ and R₂ form, together with the carbon atom which bears them, a heterocyclic group selected from a tetrahydrofuranyl or tetrahydropyranyl group, it being possible for said heterocyclic group to be fused with a phenyl group.

Among the compounds of formula (I) which are subjects of the invention, mention may be made of a subgroup of compounds for which R₃ is:
either a linear or branched $C_1$-$C_7$ alkyl group or a $C_3$-$C_7$ alkyl group in which at least 3 carbon atoms are cyclized, said alkyl group being optionally substituted with one or more groups selected from hydroxyl, alkoxy, —NRR', haloalkyl and —SO₂—($C_1$-$C_4$)alkyl groups, where R and R' are as defined hereinafter;
or a —(CH₂)$_n$-heterocyclic group, where n=0, 1, 2 or 3 and where the heterocyclic group comprises between 4 and 8 members and comprises at least one heteroatom selected from N and O atoms, where said heterocyclic group is optionally substituted with an oxo group,
or a —(CH₂)$_n$-heteroaryl group, where n=0 or 1 and where the heteroaryl group comprises 5 or 6 members and comprises one or more nitrogen heteroatoms.

More particularly, among the compounds of formula (I) which are subjects of the invention, mention may be made of a subgroup of compounds for which R₃ is a $C_3$-$C_7$ alkyl group in which at least 3 carbon atoms are cyclized, selected from cyclopropyl, cyclobutyl, cyclopentyl, cyclohexyl and methylenecyclopropyl groups.

More particularly, among the compounds of formula (I) which are subjects of the invention, mention may be made of a subgroup of compounds for which R₃ is a —(CH₂)$_n$-heterocyclic group, where n=0, 1, 2 or 3 and where the heterocyclic group is selected from tetrahydropyranyl, tetrahydrofuranyl and pyrrolidinyl groups.

More particularly, among the compounds of formula (I) which are subjects of the invention, mention may be made of a subgroup of compounds for which R₃ is a —(CH₂)$_n$-heteroaryl group, where n=1 and where the heteroaryl group is a pyridinyl group.

Among the compounds of formula (I) which are subjects of the invention, mention may be made of a subgroup of compounds for which R₄ is a $C_1$-$C_4$ alkyl group or a $C_1$-$C_4$ alkoxy group.

Among the compounds of formula (I) which are subjects of the invention, mention may be made of a subgroup of compounds for which R and R' are each a linear or branched $C_1$-$C_4$ alkyl group.

Among the compounds which are subjects of the invention, mention may in particular be made of the following compounds:
2-amino-1-ethyl-7-(3-hydroxy-3-methylbut-1-yn-1-yl)-N-methyl-4-oxo-1,4-dihydro-1,8-naphthyridine-3-carboxamide
(±)-2-amino-1-ethyl-7-[(1-hydroxycyclopentyl)ethynyl]-N-methyl-4-oxo-1,4-dihydro-1,8-naphthyridine-3-carboxamide
(±)-2-amino-1-ethyl-7-(3-hydroxybut-1-yn-1-yl)-N-methyl-4-oxo-1,4-dihydro-1,8-naphthyridine-3-carboxamide
(±)-2-amino-1-ethyl-7-(3-hydroxy-3-methylpent-1-yn-1-yl)-N-methyl-4-oxo-1,4-dihydro-1,8-naphthyridine-3-carboxamide
(±)-2-amino-1-ethyl-7-(3-hydroxy-4-methoxy-3-methylbut-1-yn-1-yl)-N-methyl-4-oxo-1,4-dihydro-1,8-naphthyridine-3-carboxamide
(±)-2-amino-7-(3-cyclopentyl-3-hydroxyprop-1-yn-1-yl)-1-ethyl-N-methyl-4-oxo-1,4-dihydro-1,8-naphthyridine-3-carboxamide
(±)-2-amino-7-(3-cyclopropyl-3-hydroxyprop-1-yn-1-yl)-1-ethyl-N-methyl-4-oxo-1,4-dihydro-1,8-naphthyridine-3-carboxamide
±2-amino-1-ethyl-7-[(1-hydroxycyclobutyl)ethynyl]-N-methyl-4-oxo-1,4-dihydro-1,8-naphthyridine-3-carboxamide
(±)-2-amino-7-(3,4-dihydroxy-3-methylbut-1-yn-1-yl)-1-ethyl-N-methyl-4-oxo-1,4-dihydro-1,8-naphthyridine-3-carboxamide
±2-amino-1-ethyl-7-[3-hydroxy-4-methoxy-3-(methoxymethyl)but-1-yn-1-yl]-N-methyl-4-oxo-1,4-dihydro-1,8-naphthyridine-3-carboxamide
(±)-2-amino-1-(cyclopropylmethyl)-7-(3-hydroxy-4-methoxy-3-methylbut-1-yn-1-yl)-N-methyl-4-oxo-1,4-dihydro-1,8-naphthyridine-3-carboxamide
(±)-2-amino-1-ethyl-7-(3-hydroxy-3-phenylbut-1-yn-1-yl)-N-methyl-4-oxo-1,4-dihydro-1,8-naphthyridine-3-carboxamide (±)-2-amino-1-ethyl-7-[3-hydroxy-3-(3-thienyl)but-1-yn-1-yl]-N-methyl-4-oxo-1,4-dihydro-1,8-naphthyridine-3-carboxamide (±)-2-amino-1-ethyl-7-[3-hydroxy-3-(3-methoxyphenyl)but-1-yn-1-yl]-N-methyl-4-oxo-1,4-dihydro-1,8-naphthyridine-3-carboxamide (±)-2-amino-1-ethyl-7-[3-hydroxy-3-(4-methoxyphenyl)but-1-yn-1-yl]-N-methyl-4-oxo-1,4-dihydro-1,8-naphthyridine-3-carboxamide (±)-2-amino-7-(3-hydroxy-4-methoxy-3-methylbut-1-yn-1-yl)-1-(3-methoxypropyl)-N-methyl-4-oxo-1,4-dihydro-1,8-naphthyridine-3-carboxamide (±)-2-amino-1-cyclopentyl-7-(3-hydroxy-4-methoxy-3-methylbut-1-yn-1-yl)-N-methyl-4-oxo-1,4-dihydro-1,8-naphthyridine-3-carboxamide (±)-2-amino-7-(3-hydroxy-4-methoxy-3-methylbut-1-yn-1-yl)-1-isopropyl-N-methyl-4-oxo-1,4-dihydro-1,8-naphthyridine-3-carboxamide (±)-2-amino-7-(3-hydroxy-4-methoxy-3-methylbut-1-yn-1-yl)-1-isobutyl-N-methyl-4-oxo-1,4-dihydro-1,8-naphthyridine-3-carboxamide ±2-amino-7-(3-hydroxy-3-methylbut-1-yn-1-yl)-1-(3-methoxypropyl)-N-methyl-4-oxo-1,4-dihydro-1,8-naphthyridine-3-carboxamide (±)-2-amino-1-ethyl-7-(3-hydroxy-4-methoxy-3-phenyl but-1-yn-1-yl)-N-methyl-4-oxo-1,4-dihydro-1,8-naphthyridine-3-carboxamide (±)-2-amino-1-(tetrahydropyran-4-yl)-7-(3-hydroxy-4-methoxy-3-methylbut-1-yn-1-yl)-N-methyl-4-oxo-1,4-dihydro-1,8-naphthyridine-3-carboxamide (±)-2-amino-1-cyclohexyl-7-(3-hydroxy-4-methoxy-3-methylbut-1-yn-1-yl)-N-methyl-4-oxo-1,4-dihydro-1,8-naphthyridine-3-carboxamide (±)-2-amino-1-ethyl-7-[3-hydroxy-3-(1,3-thiazol-2-yl)but-1-yn-1-yl]-N-methyl-4-oxo-1,4-dihydro-1,8-naphthyridine-3-carboxamide (±)-2-amino-1-ethyl-7-[3-hydroxy-3-(methoxymethyl)pent-1-yn-1-yl]-N-methyl-4-oxo-1,4-dihydro-1,8-naphthyridine-3-carboxamide (±)-2-amino-7-(3-hydroxy-4-methoxy-3-methylbut-1-yn-1-yl)-N-methyl-4-oxo-1-[3-(2-oxopyrrolidin-1-yl)propyl]-1,4-dihydro-1,8-naphthyridine-3-carboxamide (±)-2-amino-7-(3-hydroxy-4-methoxy-3-methylbut-1-yn-1-yl)-N-methyl-4-oxo-1-propyl-1,4-dihydro-1,8-naphthyridine-3-carboxamide (±)-2-amino-7-(3-hydroxy-4-methoxy-3-methylbut-1-yn-1-yl)-N-methyl-4-oxo-1-(2,2,2-trifluoroethyl)-1,4-dihydro-1,8-naphthyridine-3-carboxamide (±)-2-amino-7-(3-hydroxy-3-methylbut-1-yn-1-yl)-N-methyl-4-oxo-1-(tetrahydrofuran-2-ylmethyl)-1,4-dihydro-1,8-naphthyridine-3-carboxamide (±)-2-amino-7-(3-hydroxy-4-methoxy-3-methylbut-1-yn-1-yl)-N-methyl-4-oxo-1-(pyridin-2-ylmethyl)-1,4-dihydro-1,8-naphthyridine-3-carboxamide (±)-2-amino-1-ethyl-7-(3-hydroxy-3-pyrazin-2-ylbut-1-yn-1-yl)-N-methyl-4-oxo-1,4-dihydro-1,8-naphthyridine-3-carboxamide (±)-2-amino-7-(3-cyclopropyl-3-hydroxy-4-methoxybut-yn-1-yl)-1-ethyl-N-methyl-4-oxo-1,4-dihydro-1,8-naphthyridine-3-carboxamide (±)-2-amino-1-ethyl-7-[3-hydroxy-3-(2-thienyl)but-1-yn-1-yl]-N-methyl-4-oxo-1,4-dihydro-1,8-naphthyridine-3-carboxamide (±)-2-amino-1-ethyl-7-[3-hydroxy-3-(2-methoxyphenyl)but-1-yn-1-yl]-N-methyl-4-oxo-1,4-dihydro-1,8-naphthyridine-3-carboxamide (±)-2-amino-1-cyclopentyl-7-(3,4-dihydroxy-3-methylbut-1-yn-1-yl)-N-methyl-4-oxo-1,4-dihydro-1,8-naphthyridine-3-carboxamide (±)-2-amino-7-(4-ethoxy-3-hydroxy-3-methylbut-1-yn-1-yl)-1-ethyl-N-methyl-4-oxo-1,4-dihydro-1,8-naphthyridine-3-carboxamide (±)-2-amino-1-(trans-4-hydroxycyclohexyl)-7-(3-hydroxy-4-methoxy-3-methylbut-1-yn-1-yl)-N-methyl-4-oxo-1,4-dihydro-1,8-naphthyridine-3-carboxamide (±)-2-amino-7-(3-hydroxy-4-methoxy-3-methylbut-1-yn-1-yl)-N-methyl-1-[3-(methylsulphonyl)propyl]-4-oxo-1,4-dihydro-1,8-naphthyridine-3-carboxamide (−)-2-amino-1-(cyclopropylmethyl)-7-(3-hydroxy-4-methoxy-3-methylbut-1-yn-1-yl)-N-methyl-4-oxo-1,4-dihydro-1,8-naphthyridine-3-carboxamide (+)-2-amino-1-(cyclopropylmethyl)-7-(3-hydroxy-4-methoxy-3-methylbut-1-yn-1-yl)-N-methyl-4-oxo-1,4-dihydro-1,8-naphthyridine-3-carboxamide (+)-2-amino-7-(3,4-dihydroxy-3-methylbut-1-yn-1-yl)-1-ethyl-N-methyl-4-oxo-1,4-dihydro-1,8-naphthyridine-3-carboxamide (−)-2-amino-7-(3,4-dihydroxy-3-methylbut-1-yn-1-yl)-1-ethyl-N-methyl-4-oxo-1,4-dihydro-1,8-naphthyridine-3-carboxamide (−)-2-amino-1-ethyl-7-(3-hydroxy-3-phenylbut-1-yn-1-yl)-N-methyl-4-oxo-1,4-dihydro-1,8-naphthyridine-3-carboxamide (+)-2-amino-1-ethyl-7-(3-hydroxy-3-phenylbut-1-yn-1-yl)-N-methyl-4-oxo-1,4-dihydro-1,8-naphthyridine-3-carboxamide (−)-2-amino-7-(3-hydroxy-4-methoxy-3-methylbut-1-yn-1-yl)-1-(3-methoxypropyl)-N-methyl-4-oxo-1,4-dihydro-1,8-naphthyridine-3-carboxamide (+)-2-amino-7-(3-hydroxy-4-methoxy-3-methylbut-1-yn-1-yl)-1-(3-methoxypropyl)-N-methyl-4-oxo-1,4-dihydro-1,8-naphthyridine-3-carboxamide (−)-2-amino-1-cyclopentyl-7-(3-hydroxy-4-methoxy-3-methylbut-1-yn-1-yl)-N-methyl-4-oxo-1,4-dihydro-1,8-naphthyridine-3-carboxamide (+)-2-amino-1-cyclopentyl-7-(3-hydroxy-4-methoxy-3-methylbut-1-yn-1-yl)-N-methyl-4-oxo-1,4-dihydro-1,8-naphthyridine-3-carboxamide (−)-2-amino-7-(3-hydroxy-4-methoxy-3-methylbut-1-yn-1-yl)-1-isopropyl-N-methyl-4-oxo-1,4-dihydro-1,8-naphthyridine-3-carboxamide (+)-2-amino-7-(3-hydroxy-4-methoxy-3-methylbut-1-yn-1-yl)-1-isopropyl-N-methyl-4-oxo-1,4-dihydro-1,8-naphthyridine-3-carboxamide (−)-2-amino-1-cyclohexyl-7-(3-hydroxy-4-methoxy-3-methylbut-1-yn-1-yl)-N-methyl-4-oxo-1,4-dihydro-1,8-naphthyridine-3-carboxamide (+)-2-amino-1-cyclohexyl-7-(3-hydroxy-4-methoxy-3-methylbut-1-yn-1-yl)-N-methyl-4-oxo-1,4-dihydro-1,8-naphthyridine-3-carboxamide (−)-2-amino-1-ethyl-7-(3-hydroxy-4-methoxy-3-methylbut-1-yn-1-yl)-N-methyl-4-oxo-1,4-dihydro-1,8-naphthyridine-3-carboxamide (+)-2-amino-1-ethyl-7-(3-hydroxy-4-methoxy-3-methylbut-1-yn-1-yl)-N-methyl-4-oxo-1,4-dihydro-1,8-naphthyridine-3-carboxamide (−)-2-amino-7-(3-hydroxy-4-methoxy-3-methylbut-1-yn-1-yl)-N-methyl-4-oxo-1-propyl-1,4-dihydro-1,8-naphthyridine-3-carboxamide (+)-2-amino-7-(3-hydroxy-4-methoxy-3-methylbut-1-yn-1-yl)-N-methyl-4-oxo-1-propyl-1,4-dihydro-1,8-naphthyridine-3-carboxamide (−)-2-amino-7-(3-hydroxy-4-methoxy-3-methylbut-1-yn-1-yl)-N-methyl-4-oxo-1-(2,2,2-trifluoroethyl)-1,4-dihydro-1,8-naphthyridine-3-carboxamide (+)-2-amino-7-(3-hydroxy-4-methoxy-3-methylbut-1-yn-1-yl)-N-methyl-4-oxo-1-(2,2,2-trifluoroethyl)-1,4-dihydro-1,8-naphthyridine-3-carboxamide (+)-2-amino-1-ethyl-7-[3-hydroxy-3-(methoxymethyl)pent-1-yn-1-yl]-N-methyl-4-oxo-1,4-dihydro-1,8-naphthyridine-3-carboxamide (−)-2-amino-1-ethyl-7-[3-hydroxy-3-(methoxymethyl)pent-1-yn-1-yl]-N-methyl-4-oxo-1,4-dihydro-1,8-naphthyridine-3-carboxamide (+)-2-amino-1-ethyl-7-[3-hydroxy-3-(3-thienyl)but-1-yn-1-yl]-N-methyl-4-oxo-1,4-dihydro-1,8-naphthyridine-3-carboxamide (−)-2-amino-1-ethyl-7-[3-hydroxy-3-(3-thienyl)but-1-yn-1-yl]-N-methyl-4-oxo-1,4-dihydro-1,8-naphthyridine-3-carboxamide In accordance with the invention, the compounds of formula (I) can be prepared according to the process presented in scheme 1.

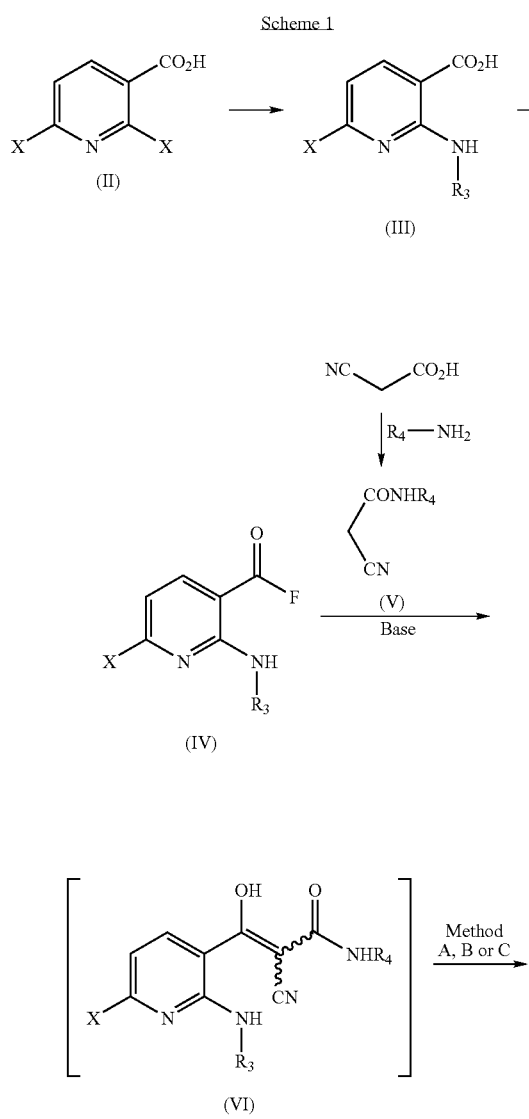

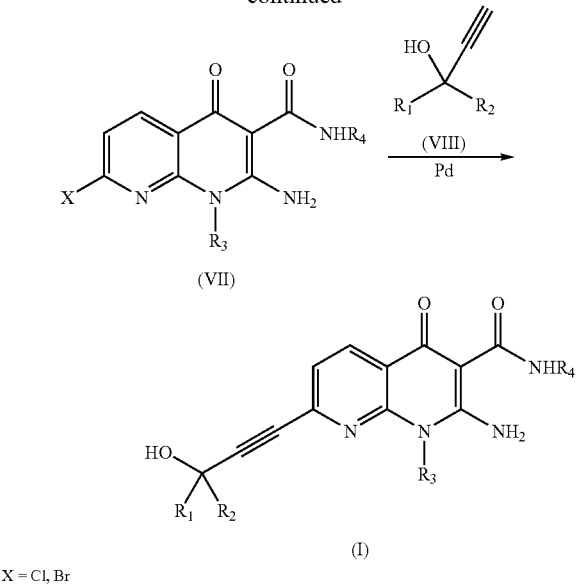

X = Cl, Br

According to Scheme 1, a 2,6-dihalonicotinic acid of formula (II), where the groups X are halogen atoms (preferably chlorine or bromine), and which is either commercially available or prepared according to the methods known to those skilled in the art, is monosubstituted at position 2 with an amine of formula $R_3$—$NH_2$ (where $R_3$ is as defined above in relation to the compounds of formula (I) which are subjects of the invention), at a temperature of between 20° C. and 150° C., in a protic solvent such as an alcohol or water and, optionally, in a sealed tube. A 2-aminonicotinic derivative of formula (III) is obtained, which is converted to the acid fluoride of formula (IV) through the action of cyanuryl fluoride at ambient temperature, in the presence of a base such as triethylamine or pyridine, and in an inert solvent such as dichloromethane, as described by G. OLAH et al., in *Synthesis* (1973), 487, or by other methods known to those skilled in the art, such as those described by MUKAIYAMA and TANAKA in *Chem. Lett.* (1976), 303 or by ISHIKAWA and SASAKI in *Chem. Lett.* (1976), 1407. The acyl fluorides of formula (IV), which are highly reactive but stable, are subsequently reacted with an N-substituted cyanoacetamide of formula (V) in the presence of a strong base such as sodium hydride in an aprotic polar solvent such as dimethylformamide.

If two equivalents of sodium hydride are used, after an overnight period at ambient temperature, a β-ceto cyanoacetamide of formula (VI) is obtained, which is subsequently cyclized to an aminopyridino[2,3-b]pyridinone of formula (VII) either by heating to a temperature of between 90 and 125° C. in a polar solvent such as n-butanol, dimethyl sulphoxide or dimethylformamide (method A), or by treating at ambient temperature with a strong base such as potassium tert-butoxide in an aprotic solvent, preferably tetrahydrofuran (method B).

When two equivalents of sodium hydride are used in the step for condensation of the derivative (IV) with a derivative (V), and then a third equivalent of NaH is introduced after stirring for between 10 and 16 hours at ambient temperature, the deprotonated compound (VI) formed cyclizes in situ at this temperature with good yields, so as to directly give the aminopyridino[2,3-b]pyridone of formula (VII) (method C).

The N-alkylcyanoacetamides of formula (V) are prepared by reacting cyanoacetic acid with an alkyl chloroformate (such as ethyl chloroformate or isobutyl chloroformate) in the presence of a base such as triethylamine, at a temperature of less than or equal to 0° C., and then the mixed anhydride intermediate formed is reacted with an excess of amine of formula $R_4$—$NH_2$ (where $R_4$ is as defined above in relation to the compounds of formula (I) which are subjects of the invention).

To obtain a pyridino[2,3-b]pyridinone of formula (I), which is the subject of the present invention, the halogenated intermediate of formula (VII) is coupled, according to the methods known to those skilled in the art, with a suitable derivative of propargyl alcohol $R_1R_2CH(OH)CCH$ of formula (VIII) where $R_1$ and $R_2$ are as defined for the compound of formula (I). For example, the intermediate (VII) is used in a Sonogashira coupling reaction with the appropriate alkyne of formula (VIII) in the presence of $PdCl_2(PPh_3)_2$, copper iodide, triethylamine and dimethylformamide, at a temperature of between 80° C. and 120° C. This reaction can be carried out in a sealed tube and under microwave radiation.

If necessary, during the reaction steps presented in scheme 1, the hydroxyl group or certain reactive functions located on the groups $R_1$, $R_2$ and $R_3$ can be temporarily protected with protective groups known to those skilled in the art and as described in "Protective Groups in Organic Synthesis", Green et al., $2^{nd}$ Edition (John Wiley & Sons, Inc., New York).

In Scheme 1, the starting compounds and the reactants, when the method for preparing them is not described, are commercially available or described in the literature, or else can be prepared according to methods which are described therein or which are known to those skilled in the art.

According to another of its aspects, a subject of the invention is also the compounds of formula (VII) defined in Scheme 1. These compounds can be used as synthesis intermediates for the compounds of formula (I).

The following examples illustrate the preparation of certain compounds in accordance with the invention. These examples are not limiting and merely illustrate the present invention. The numbers of the compounds exemplified refer to those given in the table hereinafter, which illustrates the chemical structures and the physical properties of some compounds according to the invention.

The following abbreviations and empirical formulae are used:
CuI copper iodide
$CH_2Cl_2$ dichloromethane
HPLC high performance liquid chromatography
LC/MS liquid chromatography/mass spectrometry
DMF dimethylformamide
DMSO dimethyl sulphoxide
$Et_3N$ triethylamine
h hour(s)
HCl hydrochloric acid
MHz MegaHertz
MeOH methanol
$MgSO_4$ magnesium sulphate
NaCl sodium chloride
$NH_4Cl$ ammonium chloride
$NH_4OH$ ammonium hydroxide
$NaHCO_3$ sodium hydrogen carbonate
$Na_2SO_4$ sodium sulphate
ppm part(s) per million
THF tetrahydrofuran

EXAMPLE 1

2-amino-1-ethyl-7-(3-hydroxy-3-methylbut-1-yn-1-yl)-N-methyl-4-oxo-1,4-dihydro-1,8-naphthyridine-3-carboxamide (Compound No. 2)

1.1: 2-(Aminoethyl)-6-chloronicotinic acid

A solution of 18.0 g (84.4 mmol) of 2,6-dichloronicotinic acid in 180 ml of a solution of ethylamine at 70% in water is stirred at ambient temperature for 72 hours. The excess amine is then evaporated off under reduced pressure, and an aqueous solution of acetic acid at 10% is then added until the product precipitates. The beige solid is spin-filter-dried, rinsed with cold water and dried in an oven. 10.5 g of the expected product are obtained. Melting point: 158-160° C. Yield=62%.

1.2: 2-(Aminoethyl)-6-chloronicotinic acid fluoride 2 ml (24.8 mmol) of pyridine and 4.2 ml (49.8 mmol) of 2,4,6-trifluorotriazine are added to a suspension of 5.0 g (24.8 mmol) of 2-(aminoethyl)-6-chloronicotinic acid in 125 ml of dichloromethane. The mixture is stirred for 3 hours at ambient temperature and then filtered. The solid is rinsed with 50 ml of dichloromethane and the filtrate is washed twice with 60 ml of ice-cold water. The organic phase is dried over $Na_2SO_4$ and the solvent is evaporated off under reduced pressure. 5.01 g of product are obtained in the form of an orange oil. Yield=99%.

1.3: N-methylcyanoacetamide 12.28 ml (128.44 mmol) of ethyl chloroformate are added, dropwise, to a solution, cooled to −30° C., of 10.0 g (116.38 mmol) of cyanoacetic acid at 99% and 16.3 ml (116.9 mmol) of triethylamine in 100 ml of anhydrous THF, and the mixture is then stirred at −30° C. for 1 hour 30 minutes. 300 ml of methanol saturated with methylamine gas are then added dropwise and the mixture is then stirred at ambient temperature overnight. The solvents are evaporated off under reduced pressure and the product is purified by filtration over silica gel, elution being carried out with a dichloromethane:methanol (95:5) mixture. 10.0 g of product are obtained in the form of a beige solid. Melting point=99° C. Yield=87%

Method A (points 1.4 and 1.5 hereinafter).

1.4: 3-[6-Chloro-2-(ethylamino)-3-pyridinyl]-2-cyano-3-hydroxy-N-methyl-2-propenamide 3.98 g (100 mmol) of sodium hydride at 60% in mineral oil are added, in small amounts, to a solution, cooled to 0-5° C., of 9.80 g (100 mmol) of N-methylcyanoacetamide in 100 ml of anhydrous dimethylformamide. Once no more hydrogen is being given off, the mixture is stirred for 10 minutes at ambient temperature, and is then cooled again to 0-5° C. A solution of 10.09 g (49.8 mmol) of 2-(aminoethyl)-6-chloronicotinic acid fluoride in 60 ml of dimethylformamide is then added and the medium is stirred at ambient temperature overnight. 2.85 ml (49.8 mmol) of acetic acid are added and the volatile compounds are evaporated off under reduced pressure. The residue is taken up in water and the product is extracted twice with a dichloromethane:methanol (95:5) mixture and then once with an ethyl acetate:THF (2:1) mixture. The combined organic phases are dried over $MgSO_4$ and then the solvents are evaporated off under reduced pressure. 19.0 g of product are obtained, which product is used as it is in the next step.

1.5: 2-Amino-7-chloro-1-ethyl-N-methyl-4-oxo-1,4-dihydro-1,8-naphthyridine-3-carboxamide A solution of 19.0 g of the crude product obtained at the end of step 1.4 (49.8 mmol) in 600 ml of n-butanol is heated for 48 hours at 110° C. The solvent is evaporated off under reduced pressure and the solid obtained is triturated in methanol. The solid is subsequently spin-filter-dried and dried in an oven. 7.9 g of the expected product are obtained in the form of a pale yellow solid. Melting point: 283-286° C. Yield=57%.

Method C (point 1.6 hereinafter in place of 1.4 and 1.5).

1.6: 2-Amino-7-chloro-1-ethyl-N-methyl-4-oxo-1,4-dihydro-1,8-naphthyridine-3-carboxamide 0.394 g (9.95 mmol) of sodium hydride at 60% in mineral oil is added, in small amounts, to a solution, cooled to 0-5° C., of 0.483 g (4.93 mmol) of N-methylcyanoacetamide in 7 ml of anhydrous dimethylformamide. Stirring is continued at this temperature for ten minutes and then a solution of 1.0 g (4.93 mmol) of 2-(aminoethyl)-6-chloronicotinic acid fluoride in 5 ml of dimethylformamide is added. The medium is stirred overnight at ambient temperature and then 0.197 g (4.93 mmol) of sodium hydride at 60% is added in small amounts. Stirring is continued at this temperature for 10 minutes and then 0.56 ml (9.78 mmol) of acetic acid is added. 60 ml of water are then added and the solid is spin-filter-dried, rinsed with water, and then dried in an oven. 1.30 g of the expected product are obtained. Melting point: 283-284° C. MH$^+$=281. Yield=94%.

$^1$H NMR (DMSO-d6, 400 MHz): δ 11.75 (s, <1H, very broad); 11.00 (q, 1H, broad); 8.45 (d, 1H); 8.10 (s, 1H broad); 7.40 (d, 1H); 4.40 (q, 2H); 2.80 (d, 3H); 1.25 (t, 3H).

1.7: 2-Amino-1-ethyl-7-(3-methyl-3-trimethylsilanyloxybut-1-yn-1-yl)-N-methyl-4-oxo-1,4-dihydro-1,8-naphthyridine-3-carboxamide In a 2 l three-necked flask, 40.7 g of 2-amino-7-chloro-1-ethyl-N-methyl-4-oxo-1,4-dihydro-[1,8]naphthyridine-3-carboxamide (0.145 mole) and 56.2 ml of [(1,1-dimethyl-2-propynyl)oxy]trimethylsilane (0.290 mol) are successively introduced into a mixture of 365 ml of dimethylformamide and 365 ml of triethylamine. The reaction mixture is sparged with argon for 15 minutes and then 0.983 g of CuI (5.16 mmol) and 5.1 g of bis(triphenylphosphine) palladium(II) dichloride (7.2 mmol) are added successively. The reaction mixture is heated for 15 hours at 90° C. and then concentrated under a reduced vacuum. The residue is taken up in 500 ml of an ethyl acetate/NaHCO$_{3aq}$ mixture (V/V=1/1) and filtered over a celite buffer, rinsing being carried out with ethyl acetate. The aqueous phase is extracted with dichloromethane (3×50 ml) and the organic phases are then combined, dried over sodium sulphate, filtered, and concentrated under vacuum. The reaction crude is purified by silica column chromatography (elution with a dichloromethane:ethyl acetate gradient, 80:20 to 50:50, and then a dichloromethane:methanol gradient, 95:5 to 90:10) so as to give 36.2 g of expected product (yield=62.3%) and also 7.4 g of desilylated product described in the next step (yield=15.5%).

1.8: 2-Amino-1-ethyl-7-(3-hydroxy-3-methylbut-1-yn-1-yl)-N-methyl-4-oxo-1,4-dihydro-1,8-naphthyridine-3-carboxamide 15 g of 2-amino-1-ethyl-7-(3-methyl-3-trimethylsilanyloxybut-1-yn-1-yl)-N-methyl-4-oxo-1,4-dihydro-1,8-naphthyridine-3-carboxamide (37.4 mmol) are dissolved in 815 ml of tetrahydrofuran. The solution is cooled to 0° C. and then 13.0 g of tetrabutylammonium fluoride, trihydrate (41.2 mmol) are added. The reaction mixture is stirred for 15 minutes at ambient temperature. It is evaporated to dryness and the residue is taken up in an ethyl acetate/tetrahydrofuran/water mixture. The aqueous phase is extracted with dichloromethane and then the organic phases are combined, dried over sodium sulphate, filtered, and concentrated under vacuum. 15 g of crude product are obtained, which are solubilized under hot conditions in 1 l of methanol, and then 6.75 g of activated charcoal are added and the mixture is stirred at 70° C. for 5 hours. The mixture is filtered over celite and, after evaporation under vacuum, 11.9 g of expected product are obtained in the form of a white solid.

Melting point=255° C. MH$^+$=329. Yield=82.9%.

$^1$H NMR (DMSO-d6, 400 MHz, δ in ppm): δ 11.75 (s, <1H, very broad); 11.00 (q, 1H, broad); 8.40 (d, 1H); 8.00 (s, 1H, broad); 7.40 (d, 1H); 5.62 (s, 1H, broad); 4.4 (q, 2H); 2.75 (d, 3H); 1.45 (s, 6H); 1.20 (t, 3H).

EXAMPLE 2

(±)-2-Amino-1-ethyl-7-[(3-hydroxytetrahydrofuran-3-yl)ethynyl]-N-methyl-4-oxo-1,4-dihydro-1,8-naphthyridine-3-carboxamide (Compound No. 7)

2.1: (±)-3-Ethynyltetrahydro-3-furanol

A solution of 3-oxotetrahydrofuran (4.97 mmol; preparation described in Tetrahedron 1991, 47, 6975-6982) in 20 ml of tetrahydrofuran is added to 20 ml of a commercially available solution of 0.5 M ethynylmagnesium bromide in tetrahydrofuran (10 mmol, Aldrich) cooled beforehand to 0° C. The mixture is then stirred for 4 hours at ambient temperature and a saturated solution of NH$_4$Cl$_{aq}$ is added. The mixture is extracted with ethyl acetate and the organic phases are then combined, washed with a saturated solution of NaCl$_{aq}$, dried over sodium sulphate, filtered, and concentrated under vacuum. After purification by silica column chromatography, 319 mg (2.79 mmol) of (±)-3-ethynyltetrahydro-3-furanol are obtained in the form of a yellow oil with a yield of 57%.

2.2: (±)-2-Amino-1-ethyl-7-[(3-hydroxytetrahydrofuran-3-yl)ethynyl]-N-methyl-4-oxo-1,4-dihydro-1,8-naphthyridine-3-carboxamide A suspension of 0.3 g (2.24 mmol) of 2-amino-7-chloro-1-ethyl-N-methyl-4-oxo-1,4-dihydro[1,8]naphthyridine-3-carboxamide in 17 ml of a dimethylformamide/triethylamine mixture (V/V; 2/1) is placed in a 10 ml microwave tube. This suspension is sparged with argon for 10 minutes and then 0.319 g (2.79 mmol) of (±)-3-ethynyltetrahydro-3-furanol, 0.043 g of CuI (0.23 mmol) and 0.079 g of bis(triphenylphosphine) palladium(II)dichloride (0.11 mmol) are successively added.

The sealed tube is placed in a microwave (CEM apparatus, Discover model) and the mixture is heated under pressure at 90° C. for 60 minutes (P=100 W) and then cooled and evaporated to dryness. The residue is taken up with ethyl acetate and the organic phase is washed successively with saturated NaHCO$_{3aq}$ and then saturated NaCl$_{aq}$, dried over sodium sulphate, filtered, and concentrated under vacuum. The residue obtained is purified by silica chromatography (elution with a dichloromethane:methanol gradient, 98:2 to 95:5). 0.412 g of the expected product is obtained in the form of a pale yellow solid.

Melting point=253° C. MH$^+$=357. Yield=52%.

$^1$H NMR (DMSO-d6, 400 MHz, δ in ppm): δ 11.75 (s, <1H, very broad); 11.00 (q, 1H, broad); 8.45 (d, 1H); 8.00 (s, 1H, broad); 7.4 (d, 1H); 5.6 (d, 1H); 4.55-4.30 (m, 3H); 3.95-3.80 (m, 4H); 2.8 (d, 3H); 2.20 (m, 1H); 1.9-1.35 (m, 8H); 1.25 (t, 3H).

EXAMPLE 3

(±)-2-Amino-1-ethyl-7-(3-hydroxy-4-methoxy-3-methylbut-1-yn-1-yl)-N-methyl-4-oxo-1,4-dihydro-1,8-naphthyridine-3-carboxamide (Compound No. 8)

3.1: Preparation of (±)-1-methoxy-2-methyl-3-butyn-2-ol 1400 ml (0.7 mol) of a commercially available solution of 0.5 M ethynyl magnesium chloride (or bromide) in tetrahydrofuran are run into a three-necked flask under argon. The solution is cooled to 2° C. with an ice bath and a solution of 30 g (0.327 mol) of methoxyacetone in 600 ml of tetrahydrofuran is added slowly (exothermic). The mixture is stirred for 1 hour at 2° C. and is then poured over an ice/saturated NH$_4$Cl$_{aq}$ mixture. The subsequent mixture is extracted with ether and the organic phases are then combined, dried over sodium sulphate, filtered, and concentrated under limited vacuum. The expected product is obtained in the form of 38 g of a brown oil (quantitative crude yield), which is used without subsequent purification in the next step.

3.2: (±)-2-Amino-1-ethyl-7-(3-hydroxy-4-methoxy-3-methylbut-1-yn-1-yl)-N-methyl-4-oxo-1,4-dihydro-1,8-naphthyridine-3-carboxamide A suspension of 3 g (10.69 mmol) of 2-amino-7-chloro-1-ethyl-N-methyl-4-oxo-1,4-dihydro[1,8]naphthyridine-3-carboxamide in 20 ml of a DMF/Et$_3$N mixture (V/V; 1/1) is placed in an 80 ml microwave tube. This suspension is sparged with argon for 10 minutes and then 1.83 g of (±)-1-methoxy-2-methyl-3-butyn-2-ol (16.03 mmol), 0.081 g of CuI (0.43 mmol) and 0.375 g of bis(triphenylphosphine) palladium(II)dichloride (0.53 mmol) are successively added.

The sealed tube is placed in a microwave oven (CEM apparatus, Discover model) and the mixture is heated under pressure at 90° C. for 60 minutes (P=100 W) and then cooled and evaporated to dryness. The residue is taken up in an ethyl acetate/THF mixture and then washed with a 0.1N aqueous HCl solution. The organic phase is dried over sodium sulphate, filtered, and concentrated under vacuum.

The residue obtained is purified by silica chromatography (solid deposit; elution with a cyclohexane:ethyl acetate gradient, 30:70 to 20:80). 2.49 g of the expected product are obtained in the form of a pale yellow solid.

The product can be recrystallized from ethanol, so as to give white crystals.

Melting point=211° C. MH$^+$=358. Yield=65%.

$^1$H NMR (DMSO-d6, 400 MHz, δ in ppm): δ 11.75 (s, <1H, very broad); 11.00 (q, 1H, broad); 8.45 (d, 1H); 8.00 (s, 1H, broad); 7.4 (d, 1H); 5.8 (s, 1H); 4.4 (q, 2H); 3.5-3.3 (m+s, 5H); 2.8 (d, 3H); 1.45 (s, 3H); 1.2 (t, 3H).

EXAMPLE 4

(±)-2-Amino-7-(3-cyclopentyl-3-hydroxyprop-1-yn-1-yl)-1-ethyl-N-methyl-4-oxo-1,4-dihydro-1,8-naphthyridine-3-carboxamide (Compound No. 10)

4.1: (±)-1-Cyclopentylprop-2-yn-1-ol

A solution of 0.87 ml of cyclopentanecarboxaldehyde (8.15 mmol; Aldrich) in 10 ml of tetrahydrofuran is added to 18 ml of a commercially available 0.5 M solution of ethynylmagnesium bromide in tetrahydrofuran (10 mmol, Aldrich) cooled beforehand to 0° C. The mixture is then stirred for 2 hours at ambient temperature and a saturated solution of NH$_4$Cl$_{aq}$ is added. The mixture is extracted with ethyl acetate and the organic phases are then combined, washed with a saturated solution of NaCl$_{aq}$, dried over sodium sulphate, filtered, and concentrated under vacuum. 0.931 g of (±)-1-cyclopentylprop-2-yn-1-ol is obtained in the form of a light brown oil with a yield of 92%.

4.2: (±)-2-Amino-7-(3-cyclopentyl-3-hydroxyprop-1-yn-1-yl)-1-ethyl-N-methyl-4-oxo-1,4-dihydro-1,8-naphthyridine-3-carboxamide A suspension of 1 g (3.56 mmol) of 2-amino-7-chloro-1-ethyl-N-methyl-4-oxo-1,4-dihydro[1,8]naphthyridine-3-carboxamide in 25 ml of a dimethylformamide/triethylamine mixture (V/V; 2.5/1) is placed in a 10 ml microwave tube. This suspension is sparged with argon for 10 minutes and then 0.931 g (7.5 mmol) of (±)-1-cyclopentylprop-2-yn-1-ol, 0.068 g of CuI (0.36 mmol) and 0.125 g of bis(triphenylphosphine) palladium(II)dichloride (0.18 mmol) are successively added.

The sealed tube is placed in a microwave oven (CEM apparatus, Discover model) and the mixture is heated under pressure at 80° C. for 17 minutes (P=50 W). The mixture is evaporated to dryness and the residue is then taken up with ethyl acetate. The organic phase is washed successively with saturated NaHCO$_{3aq}$ and then saturated NaCl$_{aq}$, dried over sodium sulphate, filtered, and concentrated under vacuum. The residue obtained is purified by silica chromatography (elution with a dichloromethane:methanol gradient, 98:2 to 95:5). 0.73 g of the expected product is obtained in the form of a pale yellow solid.

Melting point=253° C. MH$^+$=369. Yield=56%.

$^1$H NMR (DMSO-d6, 400 MHz, δ in ppm): δ 11.75 (s, <1H, very broad); 11.00 (q, 1H, broad); 8.45 (d, 1H); 8.00 (s, 1H, broad), 7.45 (d, 1H); 6.05 (s, 1H); 4.4 (q, 2H); 3.95-3.80 (m, 4H); 2.8 (d, 3H); 2.35-2.10 (m, 2H); 1.45 (s, 3H); 1.25 (t, 3H).

EXAMPLE 5

(±)-2-amino-7-(3-hydroxy-4-methoxy-3-methylbut-1-yn-1-yl)-N-methyl-4-oxo-1-(pyridin-2-ylmethyl)-1,4-dihydro-1,8-naphthyridine-3-carboxamide (Compound No. 47)

5.1: 6-Chloro-2-[(pyridin-2-ylmethyl)amino]nicotinic acid 4 g of 2,6-dichloronicotinic acid (20.83 mmol, Aldrich) and 10.74 ml of 2-(aminomethyl)pyridine (104.17 mmol) are placed in an 80 ml sealed tube containing 40 ml of tert-butanol. The mixture is heated at 100° C. overnight and evaporated to dryness. The residue is taken up in water and the mixture is acidified by pouring in an aqueous solution of acetic acid at 10%. The precipitate is isolated by filtration and, after drying in an oven under a reduced vacuum, 4.35 g of expected product are obtained in the form of a yellow powder (yield=79%).

5.2: 6-Chloro-2-[(pyridin-2-ylmethyl)amino]nicotinoyl fluoride 2.27 ml of triethylamine (16.31 mmol) and 1.65 ml of 2,4,6-trifluorotriazine (19.57 mmol) are added successively to a suspension of 4.3 g of 6-chloro-2-[(pyridin-2-ylmethyl)amino]nicotinic acid (16.31 mmol) in 90 ml of dichloromethane. The mixture is stirred for 1 hour at ambient temperature and then a dichloromethane/ice-cold water mixture is added. The organic phase is washed 3 times with ice-cold $NaHCO_{3aq}$ and then dried over $Na_2SO_4$, filtered, and concentrated under vacuum. 3.97 g of expected product are obtained in the form of an orange solid. Yield=92%.

5.3: 2-Amino-7-chloro-N-methyl-4-oxo-1-(pyridin-2-ylmethyl)-1,4-dihydro-1,8-naphthyridine-3-carboxamide 1.12 g (28.06 mmol) of sodium hydride at 60% in mineral oil are added, fractionwise, to a solution, cooled to 0-5° C., of 1.31 g (13.36 mmol) of N-methylcyanoacetamide (prepared according to 1.3) in 20 ml of anhydrous dimethylformamide. Stirring is continued at this temperature for ten minutes and then a solution of 3.55 g (4.93 mmol) of 6-chloro-2-[(pyridin-2-ylmethyl)amino]nicotinoyl fluoride in 20 ml of dimethylformamide is added. The medium is stirred overnight at ambient temperature and then 0.561 g (14.03 mmol) of sodium hydride at 60% is added fractionwise. Stirring is continued at this temperature for 1 hour minutes, and then the reaction mixture is poured onto ice and the subsequent mixture is acidified to pH 5-6 with an aqueous solution of acetic acid at 10%. The precipitate is isolated by filtration and, after drying in an oven, 3.98 g of the expected product are obtained in the form of a beige solid. $MH^+$=344. Yield=87%.

$^1H$ NMR (DMSO-d6, 400 MHz, δ in ppm): δ 9.20 (s, <1H, very broad); 8.85 (s, 1H); 8.30 (m, 1H); 8.10-7.85 (m, 2H, broad); 7.80 (d, 1H); 7.75 (s, 1H, broad); 6.90 (d, 1H); 4.90 (s, 2H); 2.95 (s, 3H).

5.4: (±)-2-Amino-7-(3-hydroxy-4-methoxy-3-methylbut-1-yn-1-yl)-N-methyl-4-oxo-1-(pyridin-2-ylmethyl)-1,4-dihydro-1,8-naphthyridine-3-carboxamide hydrochloride A suspension of 1 g of 2-amino-7-chloro-N-methyl-4-oxo-1-(pyridin-2-ylmethyl)-1,4-dihydro-1,8-naphthyridine-3-carboxamide (2.91 mmol) in a mixture of 20 ml of dimethylformamide and 5.7 ml of triethylamine is placed in an 80 ml microwave tube. This suspension is sparged with argon and then 0.498 g of (±)-1-methoxy-2-methyl-3-butyn-2-ol (4.36 mmol), 0.055 g of CuI (0.29 mmol) and 0.102 g of bis(triphenylphosphine)palladium(II)dichloride (0.15 mmol) are successively added.

The sealed tube is placed in a microwave oven (CEM apparatus, Discover model) and the mixture is heated under pressure at 80° C. for 45 minutes (P=100 W) and then cooled and evaporated to dryness. The residue is taken up in ethyl acetate and water. The aqueous phase is extracted with ethyl acetate (3 times), and then the organic phases are combined, dried over sodium sulphate, filtered, and concentrated under vacuum.

The residue obtained is purified by silica chromatography (solid deposit; elution with a $CH_2Cl_2/MeOH/NH_4OHaq$ gradient, 98/2/0.2 to 95/5/0.5). After trituration in ether, 0.425 g of expected product is obtained in the form of a yellow solid.

Melting point=169° C. $MH^+$=422. Yield=35%.

$^1H$ NMR (DMSO-d6, 400 MHz, δ in ppm): δ 11.65 (s, <1H, very broad); 11.00 (q, 1H, broad); 8.50-8.35 (m, 2H); 8.00 (s, 1H, broad); 7.75 (ddd, 1H); 7.45-7.20 (m, 3H); 5.80 (s, 2H, broad); 5.70 (s, 1H); 3.45-3.25 (m+s, 5H); 2.80 (d, 3H); 1.40 (s, 3H).

EXAMPLE 6

(±)-2-Amino-1-ethyl-7-(3-hydroxy-3-pyrazin-2-yl-but-1-yn-1-yl)-N-methyl-4-oxo-1,4-dihydro-1,8-naphthyridine-3-carboxamide (Compound No. 48)

6.1: (±)-2-Pyrazin-2-ylbut-3-yn-2-ol

A 0.5 M solution of ethynylmagnesium chloride in tetrahydrofuran (31.90 mmol, Aldrich) is diluted with 50 ml of tetrahydrofuran and then cooled to 0° C. 3 g of 1-pyrazin-2-ylethanone (24.56 mmol, Lancaster) are then added in several fractions, and the mixture is stirred at 0° C. for 4 hours. The mixture is cooled once again with an ice bath and a solution of $NH_4Cl_{aq}$ is added slowly. The mixture is extracted twice with ethyl acetate and the organic phases are then combined, dried over sodium sulphate, filtered, and concentrated under vacuum. The oily residue obtained is purified by silica chromatography (elution with a cyclohexane:ethyl acetate gradient, 70:30 to 50:50) and 2.9 g of the expected product are obtained in the form of a yellow oil (yield=80%).

6.2: (±)-2-Amino-1-ethyl-7-(3-hydroxy-3-pyrazin-2-ylbut-1-yn-1-yl)-N-methyl-4-oxo-1,4-dihydro-1,8-naphthyridine-3-carboxamide A suspension of 1 g (3.56 mmol) of 2-amino-7-chloro-1-ethyl-N-methyl-4-oxo-1,4-dihydro[1,8]naphthyridine-3-carboxamide in 25 ml of a DMF/$Et_3N$ mixture (V/V; 2.5/1) is placed in a 10 ml microwave tube. This suspension is sparged with argon for 10 minutes and then 0.792 g of (±)-2-pyrazin-2-ylbut-3-yn-2-ol (5.34 mmol), 0.068 g of CuI (0.36 mmol) and 0.125 g of bis(triphenylphosphine) palladium(II)dichloride (0.18 mmol) are successively added.

The sealed tube is placed in a microwave oven (CEM apparatus, Discover model) and the mixture is heated under pressure at 80° C. for 2×45 minutes (P=50 W). After a return to ambient temperature, the mixture is evaporated to dryness and the residue is taken up with ethyl acetate. The organic phase is washed successively with saturated $NaHCO_{3aq}$ then saturated $NaCl_{aq}$, dried over sodium sulphate, filtered, and concentrated under vacuum. The residue obtained is purified by silica chromatography (elution with a dichloromethane:methanol gradient, 100:0 to 98:2). 0.2 g of the impure expected product is obtained in the form of a brown solid. A further purification is carried out by silica column chromatography (elution with a cyclohexane:ethyl acetate gradient, 20:80 to 0:100) and, finally, 0.068 g of expected product is obtained in the form of a yellow solid.

Melting point=271° C. $MH^+$=393. Yield=4.9%.

$^1H$ NMR (DMSO-d6, 400 MHz, δ in ppm): δ 11.75 (s, <1H, very broad); 11.00 (q, 1H, broad); 9.0 (s, 1H); 8.65 (m, 1H); 8.40 (d, 1H); 8.00 (s, 1H, broad); 7.40 (d, 1H); 6.85 (s, 1H); 4.4 (q, 2H); 2.75 (d, 3H); 1.80 (s, 3H); 1.20 (t, 3H).

EXAMPLE 7

(±)-2-Amino-7-(3-cyclopropyl-3-hydroxy-4-methoxybut-1-yn-1-yl)-1-ethyl-N-methyl-4-oxo-1,4-dihydro-1,8-naphthyridine-3-carboxamide (Compound No. 50)

7.1: (±)-2-Cyclopropyl-1-methoxybut-3-yn-2-ol

7.1.1: N-Methoxy-N-methyl-2-methoxyacetamide 35.96 ml of triethylamine (258 mmol), followed by a solution of 14 g of methoxyacetyl chloride (Aldrich, 129 mmol) in 250 ml of dichloromethane, are added to a solution of N-methyl-O-methylhydroxylamine hydrochloride in 250 ml of dichloromethane cooled to 0° C. The mixture is stirred for 3 hours while allowing it to return to ambient temperature. A 1N solution of $HCl_{aq}$ is added and then the organic phase is washed with water, dried over sodium sulphate, filtered, and concentrated under vacuum. 13.14 g of expected product are obtained in the form of an oil which is used without subsequent purification (crude yield=76%).

7.1.2: 1-Methoxy-4-(trimethylsilyl)but-3-yn-2-one

A solution of 14.75 ml of trimethylsilylacetylene (103.62 mmol) in 250 ml of tetrahydrofuran is cooled to −70° C. and then 64.76 ml of a 1.6 M solution of n-BuLi (103.62 mmol) in hexane are added. The mixture is stirred for 25 minutes at −70° C. and then a solution of 13.14 g of N-methoxy-N-methyl-2-methoxyacetamide (98.69 mmol) in 250 ml of tetrahydrofuran is added rapidly. During the addition, the temperature rises to −50° C., and then the cold bath is removed and the mixture is stirred for 2 hours at ambient temperature. A 1N solution of $HCl_{aq}$ is added and then extraction is carried out 4 times with ethyl acetate. The organic phases are combined, dried over sodium sulphate, filtered, and concentrated under vacuum. 13.4 g of 1-methoxy-4-(trimethylsilyl)but-3-yn-2-one are obtained in the form of a light brown oil which is used without subsequent purification (crude yield=80%).

7.1.3: (±)-2-Cyclopropyl-1-methoxy-4-(trimethylsilyl)but-3-yn-2-ol 52.85 ml of 0.5 M cyclopropylmagnesium bromide (26.43 mmol, Aldrich) are added to a solution of 3 g of 1-methoxy-4-(trimethylsilyl)but-3-yn-2-one (17.62 mmol) in 160 ml of ether. The mixture is stirred at ambient temperature overnight and is then cooled with a water/ice bath and a solution of $NH_4Cl_{aq}$ and ethyl acetate is added. The mixture is extracted 3 times with ethyl acetate and the organic phases are then combined, dried over sodium sulphate, filtered, and concentrated under vacuum. The oily residue is purified by silica column chromatography, elution being carried out with a cyclohexane:ethyl acetate gradient, 100:0 to 80:20, so as to obtain 1.9 g of (±)-2-cyclopropyl-1-methoxy-4-(trimethylsilyl)but-3-yn-2-ol in the form of an oil, with a yield of 51%.

7.1.4: (±)-2-Cyclopropyl-1-methoxybut-3-yn-2-ol 10.9 mg of potassium carbonate (0.08 mmol) are added to a solution of 1.67 g of (±)-2-cyclopropyl-1-methoxy-4-(trimethylsilyl)but-3-yn-2-ol (7.86 mmol) in methanol, and the mixture is stirred overnight at ambient temperature. The methanol is evaporated off and the residue is taken up with an ethyl acetate/water mixture. The product is extracted 3 times with ethyl acetate and the organic phases are then combined, dried over sodium sulphate, filtered, and concentrated under vacuum. 0.434 g of (±)-2-cyclopropyl-1-methoxybut-3-yn-2-ol is obtained in the form of an oil used without subsequent purification (crude yield=40%).

7.2: (±)-2-Amino-7-(3-cyclopropyl-3-hydroxy-4-methoxybut-1-yn-1-yl)-1-ethyl-N-methyl-4-oxo-1,4-dihydro-1,8-naphthyridine-3-carboxamide A suspension of 0.47 g (1.68 mmol) of 2-amino-7-chloro-1-ethyl-N-methyl-4-oxo-1,4-dihydro[1,8]naphthyridine-3-carboxamide in a mixture of 8.4 ml of dimethylformamide and 3 ml of triethylamine is placed in a 10 ml microwave tube. This suspension is sparged with argon for 10 minutes and then 0.433 g of (±)-2-cyclopropyl-1-methoxybut-3-yn-2-ol (3.09 mmol), 0.032 g of CuI (0.17 mmol) and 0.059 g of bis(triphenylphosphine)palladium(II)dichloride (0.08 mmol) are successively added.

The sealed tube is placed in a microwave oven (CEM apparatus, Discover model) and the mixture is heated under pressure at 80° C. for 30 minutes (P=50 W) and then cooled and evaporated to dryness. The residue is taken up with ethyl acetate and the organic phase is washed successively with saturated $NaHCO_{3aq}$ then saturated $NaCl_{aq}$, dried over sodium sulphate, filtered, and concentrated under vacuum. The residue obtained is purified by silica chromatography, elution being carried out with a dichloromethane:methanol gradient, 100:0 to 97:3. After trituration in ether and filtration, 0.316 g of the expected product is obtained in the form of a pale yellow solid.

Melting point=208° C. MH$^+$=385. Yield=49%.

$^1$H NMR (DMSO-d6, 400 MHz, δ in ppm): δ 11.75 (s, <1H, very broad); 11.00 (q, 1H, broad); 8.45 (d, 1H); 8.00 (s, 1H, broad); 7.40 (d, 1H); 5.60 (s, 1H); 4.4 (q, 2H); 3.50 (s, 2H); 3.40 (s, 3H); 2.75 (d, 3H); 1.20 (t, 3H); 0.6-0.3 (m, 4H).

EXAMPLE 8

(±)-2-Amino-1-cyclopentyl-7-(3,4-dihydroxy-3-methylbut-1-yn-1-yl)-N-methyl-4-oxo-1,4-dihydro-1,8-naphthyridine-3-carboxamide (Compound No. 53)

8.1: (±)-2-Methylbut-3-yne-1,2-diol

A commercially available 0.5 M solution of ethynylmagnesium chloride in tetrahydrofuran is diluted with 200 ml of tetrahydrofuran and then cooled to 0° C. A solution of hydroxyacetone in 200 ml of tetrahydrofuran is than added and the mixture is stirred at ambient temperature for 3 hours. The reaction mixture is cooled and then a solution of $NH_4Cl_{aq}$ is added. The mixture is extracted 3 times with ethyl acetate and the organic phases are then combined, dried over sodium sulphate, filtered, and concentrated under vacuum (approximately 200 mbar). Finally, 20 g of expected product are obtained in the form of a brown oil, which is used without subsequent purification (quantitative crude yield).

8.2: 2-(Aminocyclopentyl)-6-chloronicotinic acid 15 g of 2,6-dichloronicotinic acid (70.31 mmol, Aldrich) and 34.7 ml of cyclopentylamine (351.56 mmol) are placed in a sealed tube containing 40 ml of tert-butanol. The mixture is heated at 100° C. overnight and evaporated to dryness. The residue is taken up in water and the product is acidified by pouring in an aqueous solution of acetic acid at 10%, and the mixture is then extracted with choloroform. The organic phases are combined, dried over sodium sulphate, filtered, and concentrated under vacuum. The solid residue is triturated in an ether/pentane mixture so as to give 5 g of expected product in the form of an off-white solid (yield=29.5%).

8.3: 2-(Aminocyclopentyl)-6-chloronicotinic acid fluoride 0.34 ml (4.15 mmol) of pyridine and 0.53 ml (6.23 mmol) of 2,4,6-trifluorotriazine are added to a suspension of 1.0 g (4.15 mmol) of 2-(aminocyclopentyl)-6-chloronicotinic acid in 12 ml of dichloromethane. The mixture is stirred for 2 hours at ambient temperature and then diluted with dichloromethane. The organic phase is washed twice with an ice-cold solution of $NaHCO_{3aq}$ and then dried over $Na_2SO_4$, filtered, and concentrated under reduced pressure. 1 g of product is obtained in the form of a brown oil, which is used immediately in the next step. Quantitative crude yield.

Method A (point 8.4 hereinafter)

8.4: 3-[6-Chloro-2-(cyclopentylamino)-3-pyridinyl]-2-cyano-3-hydroxy-N-methyl-2-propenamide+2-amino-7-chloro-1-cyclopentyl-N-methyl-4-oxo-1,4-dihydro-1,8-naphthyridine-3-carboxamide 0.349 g (8.72 mmol) of sodium hydride at 60% in mineral oil is added, in small amounts, to a solution, cooled to 0-5° C., of 0.427 g (4.36 mmol) of N-methylcyanoacetamide (preparation described in 1.3) in 10 ml of anhydrous DMF. Once no more hydrogen is being given off, the mixture is stirred for 10 minutes at ambient temperature, and then cooled again to 0-5° C. A solution of 1.0 g (4.15 mmol) of 2-(aminocyclopentyl)-6-chloronicotinic acid fluoride in 10 ml of DMF is then added and the medium is stirred at normal temperature for 1 hour. 0.174 mg (4.35 mmol) of sodium hydride at 60% in mineral oil is added and the mixture is stirred at ambient temperature overnight. The reaction mixture is poured over an ice/0.1 N $HCl_{aq}$ mixture and the precipitate is isolated by filtration. After rinsing with water and drying in an oven, 1.2 g of a greenish solid consisting of a 2/1 mixture of 3-[6-chloro-2-(cyclopentylamino)-3-pyridinyl]-2-cyano-3-hydroxy-N-methyl-2-propenamide and of 2-amino-7-chloro-1-cyclopentyl-N-methyl-4-oxo-1,4-dihydro-1,8-naphthyridine-3-carboxamide are obtained.

Method B (point 8.5 hereinafter)

8.5: 2-Amino-7-chloro-1-cyclopentyl-N-methyl-4-oxo-1,4-dihydro-1,8-naphthyridine-3-carboxamide A commercially available 1.0 M solution of potassium tert-butoxide in tetrahydrofuran (7.48 mmol; Aldrich) is added to a solution of 1.2 g of the mixture described in 8.4 (3.74 mmol) in 40 ml of anhydrous tetrahydrofuran. The mixture is stirred for 15 minutes at ambient temperature and then a 0.1N aqueous solution of $HCl_{aq}$ is added and the mixture is extracted twice with ethyl acetate. The organic phases are dried over sodium sulphate, filtered, and concentrated under vacuum. After trituration in ether and drying in an oven, 0.53 g of expected product is obtained in the form of a yellow solid (yield=44%). Melting point=256-258° C. $MH^+$=321.

8.6: (±)-2-Amino-1-cyclopentyl-7-(3,4-dihydroxy-3-methylbut-1-yn-1-yl)-N-methyl-4-oxo-1,4-dihydro-1,8-naphthyridine-3-carboxamide 15 g of 2-amino-7-chloro-1-cyclopentyl-N-methyl-4-oxo-1,4-dihydro[1,8]-naphthyridine-3-carboxamide (53.44 mmol) and 11.11 g of (±)-2-methylbut-3-yne-1,2-diol (83.39 mmol) are introduced successively into a mixture of 267 ml of dimethylformamide and 104 ml of triethylamine in a 500 ml three-necked flask. The reaction mixture is sparged with argon for 15 minutes and then 1.02 g of CuI (5.34 mmol) and 1.87 g of bis(triphenylphosphine) palladium(II)dichloride (2.67 mmol) are successively added. The reaction mixture is heated for 30 minutes at 100° C. and then concentrated under reduced vacuum. The residue is taken up in a chloroform/water mixture and the insoluble material is filtered off. 20 g of a solid are obtained, which is purified by silica chromatography (solid deposit after solubilization in a tetrahydrofuran/methanol mixture and then elution with a dichloromethane/methanol gradient, 99:1 to 80:20) so as to give 7.5 g of expected product in the form of a beige solid.
Melting point=210.5° C. $MH^+$=385. Yield=42%.
$^1$H NMR (DMSO-d6, 400 MHz, δ in ppm): δ 11.6 (s, <1H, very broad); 11.05 (q, 1H, broad); 8.40 (d, 1H); 7.35 (d, 1H); 5.5 (s, 1H); 5.15 (m, 1H); 5.0 (t, 1H); 3.45 (m, 2H); 2.80 (d, 3H); 2.3-2.1 (m, 4H); 2.05-1.8 (m, 2H); 1.75-1.5 (m, 2H); 1.4 (s, 3H).

Table 1 which follows illustrates the chemical structures and the physical properties of some compounds of formula (I) according to the invention. In this table:
- the asterisk "*" indicates, in the case where $R_1$ and $R_2$ together form a ring (heterocycle or cycloalkyl), the carbon through which said ring is attached to the adjacent carbon of the acetylene bond,
- Me and Et are, respectively, methyl and ethyl groups,
- in the "salt" column, "-" is a compound in the form of a free base, whereas "HCl" is a compound in hydrochloride form,
- the Mp column indicates the melting point, in ° C., of the compound, and
- in the LC/MS column, the following are successively indicated: the analytical high performance liquid chromatography method used (A, B or C) and detailed below, the retention time of the compound expressed in minutes, and the $MH^+$ peak identified by mass spectrometry.

Method A:
Column: Kromasil, 50×2.1 mm, 3.5 μm
Solvent A: $H_2O$/ACN/TFA (1000/30/0.5); solvent B: ACN/TFA (1000/0.5); flow rate=0.5 ml/min
Gradient: 100/0 (0 min) to 0/100 (12 min) to 0/100 (15 min)
Detection: 220 nM
Ionization: ESI+

Method B:
Column: Gemini, 50×3 mm, 3 μm
Solvent A: $H_2O$+0.1% $HCO_2H$; solvent B: ACN+0.1% $HCO_2H$; flow rate=1 ml/min
Gradient: 95/5 (0 min) to 0/100 (5.5 min) to 0/100 (7.5 min)
Detection: 220 nM
Ionization: ESI+

Method C:
Column: Kromasil, 50×2.1 mm, 3.5 μm
Solvent A: $CH_3CO_2NH_4$ 5 mM; solvent B: ACN; flow rate=0.5 ml/min
Gradient: 100/0 (0 min) to 0/100 (13 min) to 0/100 (16 min)
Detection: 220 nM
Ionization: ESI+ in the chiral LC column, the following are successively indicated for the optically pure compounds (enantiomeric purity >95%), the analytical high performance liquid chromatography method used (D or E) and detailed below, and the retention time of the compound expressed in minutes.

Method D:
Column: Chiralpak AD-H, 250×4.6 mm, 5 μM
Solvent A: 2-propanol/TFA (1000/1); solvent B: heptane/2-propanol (1000/30)
Isocratic: 50% A+50% B
Flow rate: 0.8 ml/min
Detection: 220 nM Method E:
Column: Chiralpak AD-H, 250×4.6 mm, 5 μM
Solvent A: 2-propanol/TFA (1000/1); solvent B: heptane/2-propanol (1000/30)
Isocratic: 20% A+80% B
Flow rate: 0.8 ml/min
Detection: 220 nM in the chirality column, "/" is an achiral compound, (±) is a compound in the form of a racemic mixture, (−) is a compound in the form of the optically pure levorotatory enantiomer (enantiomeric purity >95%) and (+) is a compound in the form of the optically pure dextrorotatory enantiomer (enantiomeric purity >95%). In the case of an optically pure compound, the value of the optical rotation measured at 20° C. is indicated with, between parentheses, the concentration c of the compound and the solvent used.

In order to obtain the optically pure enantiomers, the corresponding racemic mixture is subjected to preparative chromatography on a chiral stationary phase (Chiralpak AD-H column, 250×21 mm, 5 mm) using, as mobile phase:

either $CO_2$/2-propanol (70%/30%) with a flow rate of 60 ml/min at a pressure of 100 bar or an isohexane/ethanol (70/30) mixture with 0.3% of TFA and a flow rate of 120 ml/min.

After elution and evaporation, each enantiomer is isolated, and the chemical purity and enantiomeric purity of each are determined by analytical methods known to those skilled in the art.

TABLE 1

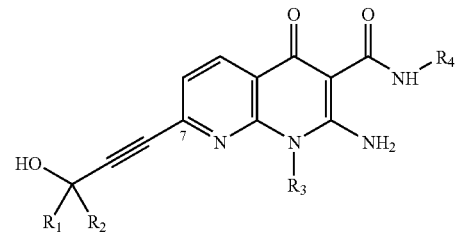

(I)

| N° | R1 | R2 | R3 | R4 | Salt | LC/MS | Chiral LC | Mp | Chirality |
|---|---|---|---|---|---|---|---|---|---|
| 1 | H | H | Et | Me | — | B 5.0 301 | — | 278 | / |
| 2 | Me | Me | Et | Me | — | C 6.3 329 | — | 256 | / |
| 3 |  | | Et | Me | — | C 6.8 355 | — | 277-279 | (±) |
| 4 | H | Me | Et | Me | — | B 5.4 315 | — | 230 | (±) |
| 5 | Me | Et | Et | Me | — | B 6.1 343 | — | 250 | (±) |
| 6 | 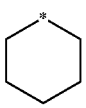 | | Et | Me | — | B 4.1 369 | — | 272 | / |
| 7 |  | | Et | Me | — | B 5.2 357 | — | 256 | (±) |

TABLE 1-continued

| # | R1 | R2 | R3 | R4 | — | Type | — | Val | Stereo |
|---|----|----|----|----|----|------|----|----|----|
| 8 | Me | ~CH(OMe)Me~ | Et | Me | — | B | — | 211 | (±) |
|   |    | 5.5 / 359 |   |   |   |   |   |   |   |
| 9 | tetrahydropyran-4-yl* |  | Et | Me | — | C | — | 275 | / |
|   | 5.9 / 371 |   |   |   |   |   |   |   |   |
| 10 | H | ~CH(cyclopentyl)~ | Et | Me | — | C | — | 253 | (±) |
|   |   | 7.7 / 369 |   |   |   |   |   |   |   |
| 11 | H | ~CH(cyclopropyl)~ | Et | Me | — | B | — | 245 | (±) |
|   |   | 5.8 / 341 |   |   |   |   |   |   |   |
| 12 | cyclobutyl* |  | Et | Me | — | C | — | 218 | / |
|   | 6.45 / 341 |   |   |   |   |   |   |   |   |
| 13 | Me | ~CH(CH2OH)~ | Et | Me | — | B | — | 207 | (±) |
|   |   | 4.6 / 345 |   |   |   |   |   |   |   |
| 14 | ~CH2OMe | ~CH(CH2OMe)~ | Et | Me | — | B | — | 199 | / |
|   |   | 3.5 / 389 |   |   |   |   |   |   |   |
| 15 | Me | ~CH(CH2OMe)~ | ~CH2CH2N(Me)2~ | Me | — | B | — | 159 | (±) |
|   |   | 3.03 / 402 |   |   |   |   |   |   |   |

TABLE 1-continued

| # | R1 | R2 | R3 | R4 | | | | mp/other | config |
|---|----|----|----|----|---|---|---|---|---|
| 16 | Me | -CH₂CH₂OMe | -CH₂CH₂OMe | Me | — | C | — | 159 | (±) |
| | | | | | | | | 6.3 389 | |
| 17 | Me | -CH₂CH₂OMe | -CH₂-cyclopropyl | Me | — | C | — | 170 | (±) |
| | | | | | | | | 6.7 385 | |
| 18 | Me | -CH₂CH₂OMe | Me | Me | — | C | — | 218-219 | (±) |
| | | | | | | | | 5.7 345 | |
| 19 | Me | -C(O)Me | Et | Me | B | — | 226 | | (±) |
| | | | | | | | | 3.7 357 | |
| 20 | Me | phenyl | Et | Me | — | C | — | 234 | (±) |
| | | | | | | | | 7.6 391 | |
| 21 | Me | -CH₂CH₂OMe | -CH₂CH₂OH | Me | — | C | — | 230 | (±) |
| | | | | | | | | 5.5 375 | |
| 22 | Me | -CH₂CH₂OMe | Et | MeO | — | B | — | 172 | (±) |
| | | | | | | | | 5.2 375 | |
| 23 | Me | 3-thienyl | Et | Me | — | C | — | 204 | (±) |
| | | | | | | | | 7.3 397 | |

TABLE 1-continued
| 24 | Me | 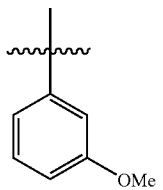 [SMILES: *c1cccc(OC)c1] | Et | Me | — | C | — | 223 | (±) |
|---|---|---|---|---|---|---|---|---|---|
| | | | | | | 7.6 421 | | | |
| 25 | Me | 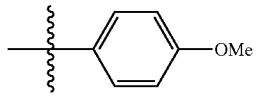 | Et | Me | — | B | — | 223.5 | (±) |
| | | | | | | 11.6 421 | | | |
| 26 | Me | 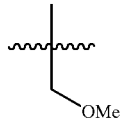 [SMILES: *COC] | 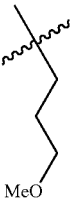 [SMILES: *CCCOC] | Me | — | C | — | 140.5 | (±) |
| | | | | | | 6.3 403 | | | |
| 27 | Me | 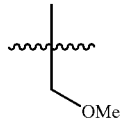 [SMILES: *COC] | 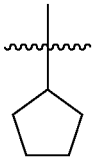 | Me | — | C | — | 180 | (±) |
| | | | | | | 7.05 399 | | | |
| 28 | Me | 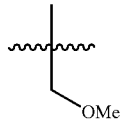 [SMILES: *COC] | 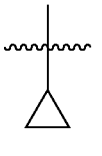 | Me | — | C | — | 175.5 | (±) |
| | | | | | | 5.9 371 | | | |
| 29 | Me | 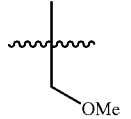 [SMILES: *COC] | 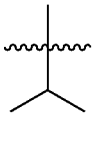 | Me | — | C | — | 159.5 | (±) |
| | | | | | | 6.1 373 | | | |
| 30 | Me | 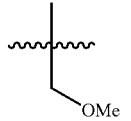 [SMILES: *COC] | 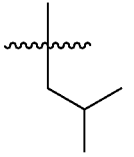 | Me | — | C | — | 195 | (±) |
| | | | | | | 6.7 387 | | | |
| 31 | Me | Me |  | Me | — | C | — | 183 | / |

TABLE 1-continued
| | | | | | | | | | |
|---|---|---|---|---|---|---|---|---|---|
| 32 | 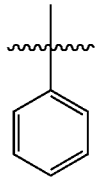 | 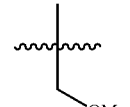 | Et | Me | — | C | — | 6.45 373 226 | (±) |
| 33 | Me | 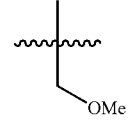 [SMILES: *COC] | 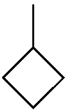 | Me | — | C | — | 7.2 421 169-170 | (±) |
| 34 | Me | 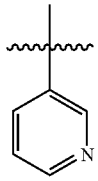 | Et | Me | HCl | C | — | 6.1 385 150-155 | (±) |
| 35 | Me | 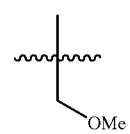 [SMILES: *COC] | Et | H | — | C | — | 5.8 392 214 | (±) |
| 36 | Me | 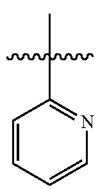 | Et | Me | HCl | C | — | 5.0 345 292-293 | (±) |
| 37 | Me | 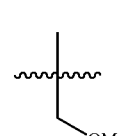 | 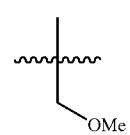 [SMILES: *COC] | Me | — | B | — | 6.1 429 301 | (±) |
| 38 | Me | 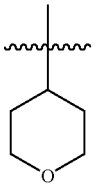 | 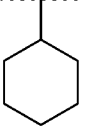 | Me | — | C | — | 5.4 415 284 | (±) |
| | | | | | | | | 6.9 413 | |

TABLE 1-continued
| | | | | | | | | | |
|---|---|---|---|---|---|---|---|---|---|
| 39 | Me | 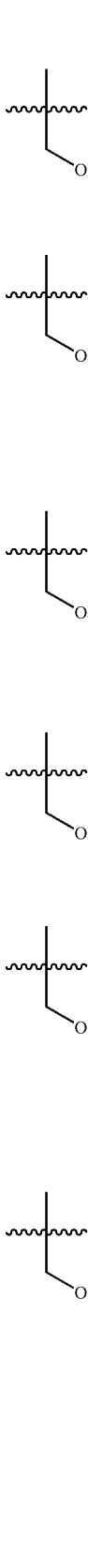 | Et | Me | — | C | — | 220.4 | (±) |
| | | | | | | | | 6.5 | |
| | | | | | | | | 398 | |
| 40 | Et | 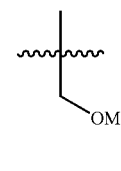 | Et | Me | — | B | — | 181.5 | (±) |
| | | | | | | | | 5.8 | |
| | | | | | | | | 373 | |
| 41 | Me | 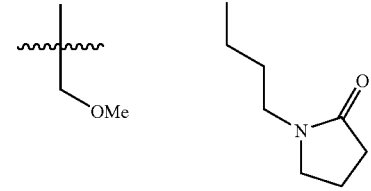 | 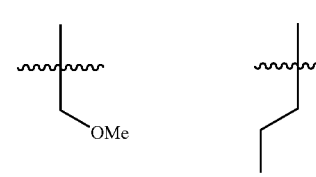 | Me | — | C | — | 181 | (±) |
| | | | | | | | | 5.9 | |
| | | | | | | | | 456 | |
| 42 | Me | | | Me | — | B | — | 175 | (±) |
| | | | | | | | | 6.14 | |
| | | | | | | | | 373 | |
| 43 | Me | | 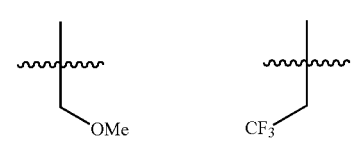 | Me | — | C | — | 222.5 | (±) |
| | | | | | | | | 6.8 | |
| | | | | | | | | 413 | |
| 44 | Me | | 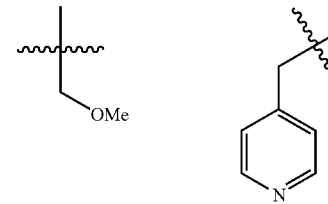 | Me | HCl | B | — | 232 | (±) |
| | | | | | | | | 4.7 | |
| | | | | | | | | 422 | |
| 45 | Me | | 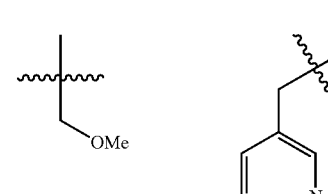 | Me | HCl | C | — | >180 | (±) |
| | | | | | | | | 6.0 | |
| | | | | | | | | 422 | |

TABLE 1-continued

| 46 | Me | Me | (tetrahydrofuran-2-ylmethyl) | Me | — | C | — | 221 | (±) |
|----|----|----|---|----|---|---|---|-----|-----|
|    |    |    |   |    |   |   |   | 6.3 |     |
|    |    |    |   |    |   |   |   | 385 |     |
| 47 | Me | CH₂OMe | (pyridin-2-ylmethyl) | Me | — | B | — | 169 | (±) |
|    |    |    |   |    |   |   |   | 5.8 |     |
|    |    |    |   |    |   |   |   | 422 |     |
| 48 | Me | (pyrazin-2-yl) | Et | Me | — | C | — | 271 | (±) |
|    |    |    |   |    |   |   |   | 5.4 |     |
|    |    |    |   |    |   |   |   | 393 |     |
| 49 | (2,3-dihydro-1,4-benzodioxin-2-yl)* | Et | Me | — | C | — | 246.5 | (±) |
|    |    |    |   |    |   |   |   | 7.2 |     |
|    |    |    |   |    |   |   |   | 419 |     |
| 50 | Me | cyclopropyl | Et | Me | — | C | — | 208 | (±) |
|    |    |    |   |    |   |   |   | 6.5 |     |
|    |    |    |   |    |   |   |   | 385 |     |
| 51 | Me | (thiophen-2-yl) | Et | Me | — | C | — | 207.5 | (±) |
|    |    |    |   |    |   |   |   | 7.2 |     |
|    |    |    |   |    |   |   |   | 397 |     |
| 52 | Me | (2-methoxyphenyl) | Et | Me | — | C | — | 223 | (±) |
|    |    |    |   |    |   |   |   | 7.45 |    |
|    |    |    |   |    |   |   |   | 421 |     |

TABLE 1-continued
| 53 | Me | 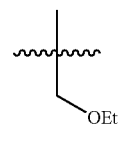 | 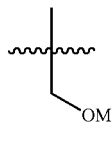 | Me | — | C | — | 210.5 | (±) |
| --- | --- | --- | --- | --- | --- | --- | --- | --- | --- |
| | | | | | | 6.0 385 | | | |
| 54 | Me | 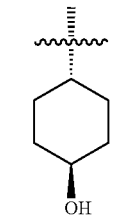 | Et | Me | — | C | — | 190 | (±) |
| | | | | | | 6.6 385 | | | |
| 55 | Me | 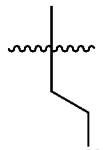 | 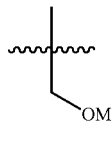 | Me | — | C | — | 236.5 | (±) |
| | | | | | | 5.6 429 | | | |
| 56 | Me | 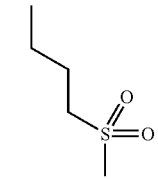 | Et | Me | — | B | — | — | (±) |
| | | | | | | 6.0 373 | | | |
| 57 | Me | 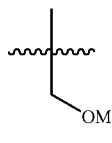 | 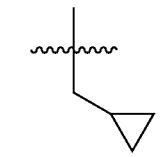 | Me | — | C | — | 194 | (±) |
| | | | | | | 6.0 451 | | | |
| 58 | Me | 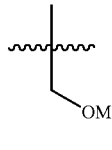 | 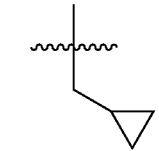 [SMILES: *CC1CC1] | Me | — | A | D | — | (−) [α]$_D$ = −7.2° (c = 0.98; MeOH) |
| | | | | | | 6.6 385 | 5.6 | | |
| 59 | Me |  |  | Me | — | A | D | — | (+) [α]$_D$ = +6.1° (c = 0.99; DMSO) |
| | | | | | | 6.8 385 | 6.7 | | |

TABLE 1-continued

| # | R1 | R2 | R3 | R4 | | | | | Optical |
|---|----|----|----|----|---|---|---|---|---------|
| 60 | Me | ‑CH(OH)‑ (wavy line to C with OH below) | Et | Me | — | A | D | — | (+) [α]$_D$ = +5.1° (c = 1; DMSO) |
| | | 4.8 345 | 12.1 | | | | | | |
| 61 | Me | ‑CH(OH)‑ (wavy line to C with OH below) | Et | Me | — | A | D | — | (−) [α]$_D$ = −4.2° (c = 0.90; DMSO) |
| | | 4.8 345 | 9.1 | | | | | | |
| 62 | Me | ‑CH(Ph)‑ (phenyl group) | Et | Me | — | A | E | — | (−) [α]$_D$ = −6.4° (c = 0.1; DMSO) |
| | | 7.6 391 | 13.7 | | | | | | |
| 63 | Me | ‑CH(Ph)‑ (phenyl group) | Et | Me | — | A | E | — | (+) [α]$_D$ = +6.7° (c = 1; DMSO) |
| | | 7.6 391 | 24.7 | | | | | | |
| 64 | Me | ‑CH(OMe)‑ | ‑CH$_2$CH$_2$CH$_2$OMe (wavy) | Me | — | A | E | — | (−) [α]$_D$ = −5.0° (c = 1; DMSO) |
| | | 6.1 403 | 14.1 | | | | | | |
| 65 | Me | ‑CH(OMe)‑ | ‑CH$_2$CH$_2$CH$_2$OMe (wavy) | Me | — | A | E | — | (+) [α]$_D$ = +4.9° (c = 1; DMSO) |
| | | 6.1 403 | 18.2 | | | | | | |
| 66 | Me | ‑CH(OMe)‑ | cyclopentyl (wavy) | Me | — | A | E | — | (−) [α]$_D$ = −3.6° (c = 0.27; DMSO) |
| | | 7.0 399 | 11.1 | | | | | | |

TABLE 1-continued

| # | R1 | R2 | R3 | R4 | | | | | |
|---|----|----|----|----|---|---|---|---|---|
| 67 | Me | (CH(OMe)-) wavy | cyclopentyl wavy | Me | — | A | E | — | (+) $[\alpha]_D = +4.9°$ (c = 1; DMSO) |
| | | | | | | 7.0 399 | 15.6 | | |
| 68 | Me | (CH(OMe)-) wavy | isopropyl wavy | Me | — | A | E | — | (−) $[\alpha]_D = −4.2°$ (c = 0.63; DMSO) |
| | | | | | | 6.3 373 | 30.9 | | |
| 69 | Me | (CH(OMe)-) wavy | isopropyl wavy | Me | — | A | E | — | (+) $[\alpha]_D = +5.3°$ (c = 0.81; DMSO) |
| | | | | | | 6.3 373 | 12.3 | | |
| 70 | Me | (CH(OMe)-) wavy | cyclohexyl wavy | Me | — | A | E | — | (−) $[\alpha]_D = −4.3°$ (c = 0.85; DMSO) |
| | | | | | | 7.4 413 | 12.2 | | |
| 71 | Me | (CH(OMe)-) wavy | cyclohexyl wavy | Me | — | A | E | — | (+) $[\alpha]_D = +2.5°$ (c = 0.99; DMSO) |
| | | | | | | 7.4 413 | 19.3 | | |
| 72 | Me | (CH(OMe)-) wavy | Et | Me | — | C | E | — | (−) $[\alpha]_D = −5.1°$ (c = 1; MeOH) |
| | | | | | | 6.1 359 | 5.4 | | |
| 73 | Me | (CH(OMe)-) wavy | Et | Me | — | C | E | — | (+) $[\alpha]_D = +5.4°$ (c = 1; MeOH) |
| | | | | | | 6.1 359 | 6.7 | | |
| 74 | Me | (CH(OMe)-) wavy | (CH(Et)-) wavy | Me | — | A | E | — | (−) $[\alpha]_D = −4.3°$ (c = 0.85; DMSO) |
| | | | | | | 6.4 373 | 12.0 | | |

TABLE 1-continued

| # | R1 | (structure) | (structure) | R | — | A | E | — | optical |
|---|----|----|----|----|----|----|----|----|----|
| 75 | Me | OMe branched | branched | Me | — | A | E | — | (+) $[\alpha]_D = +2.9°$ (c = 0.98; DMSO) |
| | | | | | | 6.35 | 31.1 | | |
| | | | | | | 373 | | | |
| 76 | Me | OMe | CF$_3$ | Me | — | A | E | — | (−) $[\alpha]_D = -2.4°$ (c = 1; DMSO) |
| | | | | | | 6.5 | 11.2 | | |
| | | | | | | 413 | | | |
| 77 | Me | OMe | CF$_3$ | Me | — | A | E | — | (+) $[\alpha]_D = +2.6°$ (c = 1.01; DMSO) |
| | | | | | | 6.5 | 31.5 | | |
| | | | | | | 413 | | | |
| 78 | Et | OMe | Et | Me | — | A | E | — | (+) $[\alpha]_D = +6.5°$ (c = 1.01; DMSO) |
| | | | | | | 6.5 | 12.4 | | |
| | | | | | | 373 | | | |
| 79 | Et | OMe | Et | Me | — | A | E | — | (−) $[\alpha]_D = -8.7°$ (c = 0.90; DMSO) |
| | | | | | | 6.4 | 21.0 | | |
| | | | | | | 373 | | | |
| 80 | Me | thiophene | Et | Me | — | A | E | — | (+) $[\alpha]_D = +1.9°$ (c = 0.40; DMSO) |
| | | | | | | 7.25 | 15.5 | | |
| | | | | | | 397 | | | |
| 81 | Me | thiophene | Et | Me | — | A | E | — | (−) $[\alpha]_D = -1.8°$ (c = 1; DMSO) |
| | | | | | | 7.3 | 25.9 | | |
| | | | | | | 397 | | | |

The compounds according to the invention were the subject of pharmacological assays for determining their inhibitory effect on the VEGFR-3 enzyme.

Measurement of the Tyrosine Kinase Activity of VEGFR-3 by ELISA

The enzymatic activity of VEGFR-3 is evaluated on an ELISA assay by measuring the intensity of phosphorylation of the substrate poly Glu-Tyr. The effect of the products is quantified by the concentration which decreases the total activity of the enzyme by 50% (IC50). To determine the IC50 values, the product is diluted in DMSO with a concentration range which extends from 3 to 1000 nM. The day before the manipulation, 125 µl of the poly Glu-Tyr substrate (250 µg/ml in 1×PBS without $Ca^{2+}$ or $Mg^{2+}$ or sodium bicarbonate) are deposited in each well of an ELISA plate (for example, an ELISA plate of the SIGMA Protein Tyrosine Kinase Assay kit, Ref. PTK-101). The plate is then covered with an adhesive film and incubated overnight at 37° C. The following day, the wells are emptied by turning the plate over, washed by adding 300 µl of buffer solution (PBS+0.05% Tween 20) and dried by further incubation of the plate for 2 h at 37° C. A 90 µl reaction mixture is deposited onto each well. This mixture contains the 1×kinase buffer to which 30 µM of ATP and the inhibitor at the desired concentration have been added. Next, 20 µl of VEGFR-3-TK (Cell signaling, Ref. 7790), diluted beforehand in the kinase buffer without ATP, are added (with the exception of the negative control wells, where 20 µl of buffer without enzyme are added). The plates are then incubated with gentle agitation at ambient temperature for 30 min. After 3 rinses with the buffer solution (300 µl/well per wash), 100 µl of anti-phosphotyrosine-HRP antibody (1/30 000) are added to each well and the plates are again incubated for 30 min at ambient temperature with gentle agitation. After 3 washes in buffer solution (300 µl/well per wash), the phosphorylation of the substrate is revealed by adding 100 µl per well of OPD substrate, 1 OPD tablet and 1 urea tablet in 20 ml of water (extemporaneous preparation in the dark). After incubation for 7 minutes at ambient temperature and in the dark, the reaction is stopped by adding 100 µl of 1.25 M (2.5N) $H_2SO_4$ per well, and the absorbance is read at 492 nm. The total activity is evaluated by the difference in optical density obtained on samples incubated in the presence (stimulated) and in the absence (non-stimulated) of VEGFR-3.

The compounds in accordance with the invention exhibit IC50 values of less than 10 µM, for most of them less than 1 µM. By way of examples, the IC50 values of some compounds of Table 1 are indicated in Table 2 below.

TABLE 2

| No. of the compound (Table 1) | IC50 (nM) |
|---|---|
| 2 | 23 |
| 3 | 46 |
| 11 | 37 |
| 12 | 21 |
| 16 | 257 |
| 24 | 6 |
| 37 | 34 |
| 46 | 40 |
| 47 | 65 |
| 60 | 43 |
| 62 | 14 |
| 70 | 5 |
| 72 | 23 |
| 80 | 2 |
| 81 | 38 |

It therefore appears that the compounds according to the invention have an inhibitory activity on the VEGFR-3 enzyme; they may therefore be used in the preparation of medicaments, in particular of medicaments which inhibit VEGFR-3.

Thus, according to another of its aspects, a subject of the invention is medicaments which comprise a compound of formula (I), or an addition salt of the latter with a pharmaceutically acceptable acid or base, or else a hydrate or a solvate, and also an enantiomer or a diastereoisomer, including a mixture thereof, of the compound of formula (I).

Another aspect of the invention comprises a combination of at least one compound according to the invention and at least one chemotherapy agent.

Specifically, the compounds of the present invention may be used alone or as a mixture with at least one chemotherapy agent that may be selected from:
  alkylating agents,
  intercalating agents,
  antimicrotubule agents,
  antimitotics,
  antimetabolites,
  antiproliferative agents,
  antibiotics,
  immunomodulatory agents,
  anti-inflammatories,
  kinase inhibitors,
  anti-angiogenic agents,
  antivascular agents,
  oestrogenic and androgenic hormones,
  and the prodrugs of the agents or derivatives mentioned above.

It is also possible to combine the compounds according to the invention with a radiation treatment.

The combinations of the compounds of the invention with the chemotherapy agents mentioned above and/or radiation are another subject of the present invention.

The chemotherapy agents mentioned above and/or the radiation may be administered simultaneously, separately or sequentially. The treatment will be adjusted by the practitioner according to the patient to be treated.

These medicaments are used therapeutically, in particular in the treatment and/or prevention:
  of cancers and metastases thereof, such as: glioblastomas, multiple myelomas, myelodysplasic syndromes, Kaposi's sarcomas, cutaneous angiosarcomas, solid tumours, lymphomas, melanomas, breast cancers, colorectal cancers, lung cancers, including non-small-cell cancers, pancreatic cancers, prostate cancers, kidney cancers, head and neck cancers, liver cancers, ovarian cancers, cancers of the respiratory tract and chest, other tumours expressing VEGFR-3 or involving a process of angiogenesis or of lymphangiogenesis,
  non-oncological proliferative diseases and pathological angiogenesis linked to VEGFR-3, such as: arthrosis, restenosis, psoriasis, hemangiomas, lymphangiomas, glaucomas, glomerulonephritis, diabetic nephropathies, nephrosclerosis, thrombotic microangiopathic syndromes, liver cirrhosis, atherosclerosis, organ transplant rejection, eye diseases involving a process of angiogenesis or of lymphangiogenesis, such as diabetic retinopathy or macular degeneration,
  or else in the treatment and prevention of inflammation (chronic or non-chronic), of infection with microorganisms and of autoimmune diseases, such as rheumatoid arthritis,
  or else in the treatment of rare diseases such as lymphangioleiomyomatosis.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected according to the pharmaceutical form and the method of administration desired, from the usual excipients which are known to those skilled in the art.

In the pharmaceutical compositions of the invention for oral, sublingual, subcutaneous, intramuscular, intravenous, topical, local, intratracheal, intranasal, transdermal or rectal administration, the active ingredient of formula (I) above, or possible salt, solvate or hydrate thereof, may be administered in unit administration form, as a mixture with conventional pharmaceutical excipients, to animals and to human beings for the treatment or prevention of the disorders or diseases above.

The appropriate unit administration forms comprise oral administration forms, such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration of a compound according to the invention in tablet form may comprise the following components:

| | |
|---|---|
| Compound according to the invention | 50.0 mg |
| Mannitol | 223.75 mg |
| Sodium croscaramellose | 6.0 mg |
| Maize starch | 15.0 mg |
| Hydroxypropylmethylcellulose | 2.25 mg |
| Magnesium stearate | 3.0 mg |

According to another its aspects, the present invention also relates to a method of treating the pathologies indicated above, which comprises the administration, to a patient, of an effective dose of a compound according to the invention, or a pharmaceutically acceptable salt, a hydrate or a solvate thereof.

What is claimed is:

1. A compound of formula (I):

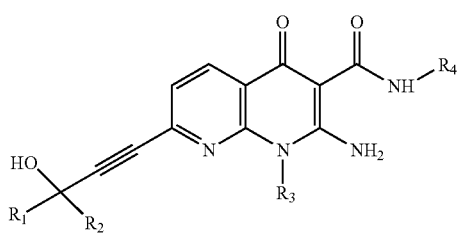

(I)

wherein:

$R_1$ and $R_2$ (1) are, independently of one another:

a hydrogen atom, a $C_1$-$C_7$ alkyl group, a —CO—($C_1$-$C_7$) alkyl group or a $C_3$-$C_8$ cycloalkyl group, where said alkyl or cycloalkyl group is optionally substituted with one or more groups selected from the group consisting of a halogen atom, hydroxyl, and alkoxy group, a phenyl group optionally substituted with one or more groups selected from the group consisting of a halogen atom, $C_1$-$C_4$ alkyl, $C_1$-$C_4$ alkoxy, hydroxyl, haloalkoxy, haloalkyl, —CN and —NRR', where R and R' are as defined below, or a heteroaryl group optionally substituted in any position, including on a nitrogen atom of said heteroaryl, with one or more groups selected from the group consisting of a halogen atom, $C_1$-$C_4$ alkyl, and —NRR', where R and R' are as defined below; or (2) form, together with the carbon atom that bears them:

a $C_4$-$C_8$ cycloalkyl group, or a 4- to 8-membered saturated heterocyclic group comprising a heteroatom selected from the group consisting of an N, O and S atom, wherein said heterocyclic group is optionally fused with a phenyl group;

$R_3$ is:

a linear or branched $C_1$-$C_7$ alkyl group or a $C_3$-$C_7$ alkyl group wherein at least 3 carbon atoms are cyclized, said alkyl group being optionally substituted with one or more groups selected from the group consisting of a halogen atom, hydroxyl, alkoxy, —NRR', -haloalkyl and —$SO_2$—($C_1$-$C_4$)alkyl, where R and R' are as defined hereinafter, a —($CH_2$)$_n$-heterocyclic group, where n=0, 1, 2 or 3 and where the heterocyclic group comprises between 4 and 8 members and comprises at least one heteroatom selected from the group consisting of an N, O and S atom, where said heterocyclic group is optionally substituted with an oxo group, or a —($CH_2$)$_n$-heteroaryl group, where n=0, 1, 2 or 3 and where the heteroaryl group comprises 5 or 6 members and comprises one or more heteroatoms selected from the group consisting of nitrogen, oxygen and sulphur; and $R_4$ is a hydrogen atom, a $C_1$-$C_4$ alkyl group or a $C_1$-$C_4$ alkoxy group;

wherein R and R' are, independently of one another, a hydrogen atom or a $C_1$-$C_4$ alkyl group;

or an acid addition salt of formula (I) thereof, or an enantiomer or diastereoisomer thereof, or a mixture thereof.

2. The compound according to claim 1, wherein:

$R_1$ and $R_2$ (1) are, independently of one another:

a hydrogen atom, a $C_1$-$C_7$ alkyl group, a —CO—($C_1$-$C_7$)alkyl group or a $C_3$-$C_8$ cycloalkyl group, where said alkyl group is optionally substituted with one or more groups selected from the group consisting of hydroxyl and alkoxy, a phenyl group optionally substituted with one or more $C_1$-$C_4$ alkoxy groups, or a heteroaryl group; or (2) form, together with the carbon atom which bears them:

a $C_4$-$C_8$ cycloalkyl group, or a 4- to 8-membered saturated heterocyclic group comprising a heteroatom selected from the group consisting of an N, O and S atom, wherein said heterocyclic group is optionally fused with a phenyl group;

$R_3$ is:

a linear or branched $C_1$-$C_7$ alkyl group or a $C_3$-$C_7$ alkyl group wherein at least 3 carbon atoms are cyclized, said alkyl group being optionally substituted with one or more groups selected from the group consisting of hydroxyl, alkoxy, —NRR', haloalkyl and —$SO_2$—($C_1$-$C_4$)alkyl, where R and R' are as defined hereinafter, a —($CH_2$)$_n$-heterocyclic group, where n=0, 1, 2 or 3 and where the heterocyclic group comprises between 4 and 8 members and comprises at least one heteroatom selected from the group consisting of an N and O atom, where said heterocyclic group is optionally substituted with an oxo group, or a —($CH_2$)$_n$-heteroaryl group, where n=0 or 1 and where the heteroaryl group comprises 5 or 6 members and comprises one or more nitrogen heteroatoms; and $R_4$ is a $C_1$-$C_4$ alkyl group or a $C_1$-$C_4$ alkoxy group;

wherein R and R' are each a linear or branched $C_1$-$C_4$ alkyl group.

3. The compound according to claim 1, wherein:

$R_1$ and $R_2$ (1) are, independently of one another:

a hydrogen atom, a $C_1$-$C_7$ alkyl group, a —CO—($C_1$-$C_7$)alkyl group or a $C_3$-$C_8$ cycloalkyl group, where said alkyl group is optionally substituted with one or more groups selected from the group consisting of hydroxyl and alkoxy, a phenyl group optionally substituted with one or more $C_1$-$C_4$ alkoxy groups, or a heteroaryl group; or (2) form, together with the carbon atom which bears them:

a $C_4$-$C_8$ cycloalkyl group, or a 4- to 8-membered saturated heterocyclic group comprising an oxygen heteroatom, wherein said heterocyclic group is optionally fused with a phenyl group;

$R_3$ is:

a linear or branched $C_1$-$C_7$ alkyl group or a $C_3$-$C_7$ alkyl group in which at least 3 carbon atoms are cyclized, said alkyl group being optionally substituted with one or more groups selected from the group consisting of hydroxyl, alkoxy, —NRR', haloalkyl and —$SO_2$—($C_1$-$C_4$)alkyl, where R and R' are as defined hereinafter, a —$(CH_2)_n$-heterocyclic group, where n=0, 1, 2 or 3 and where the heterocyclic group comprises between 4 and 8 members and comprises at least one heteroatom selected from the group consisting of an N and O atom, where said heterocyclic group is optionally substituted with an oxo group, or a —$(CH_2)_n$-heteroaryl group, where n=0 or 1 and where the heteroaryl group comprises 5 or 6 members and comprises one or more nitrogen heteroatoms; and $R_4$ is a $C_1$-$C_4$ alkyl group or a $C_1$-$C_4$ alkoxy group;

wherein R and R' are each a linear or branched $C_1$-$C_4$ alkyl group.

4. The compound according to claim 1, wherein:

$R_1$ and $R_2$ (1) are, independently of one another:

a hydrogen atom, a $C_1$-$C_7$ alkyl group or a $C_3$-$C_8$ cycloalkyl group, where said alkyl group is optionally substituted with one or more groups selected from the group consisting of hydroxyl and alkoxy, a phenyl group optionally substituted with one or more $C_1$-$C_4$ alkoxy groups, or a heteroaryl group; or (2) form, together with the carbon atom which bears them, a $C_4$-$C_8$ cycloalkyl group;

$R_3$ is:

a linear or branched $C_1$-$C_7$ alkyl group or a $C_3$-$C_7$ alkyl group in which at least 3 carbon atoms are cyclized, said alkyl group being optionally substituted with one or more groups selected from the group consisting of hydroxyl, alkoxy, haloalkyl and —$SO_2$—($C_1$-$C_4$)alkyl, a —$(CH_2)_n$-heterocyclic group, where n=0, 1, 2 or 3 and where the heterocyclic group comprises between 4 and 8 members and comprises at least one heteroatom selected from the group consisting of an N and O atom, where said heterocyclic group is optionally substituted with an oxo group, or a —$(CH_2)_n$-heteroaryl group, where n=0 or 1 and where the heteroaryl group comprises 5 or 6 members and comprises one or more nitrogen heteroatoms; and $R_4$ is a $C_1$-$C_4$ alkyl group;

wherein R and R' are each a linear or branched $C_1$-$C_4$ alkyl group.

5. The compound according to claim 1, wherein $R_1$ and $R_2$:

(1) represent, independently of one another:

a hydrogen atom, a $C_1$-$C_7$ alkyl group, a —CO—($C_1$-$C_7$)alkyl group or a $C_3$-$C_8$ cycloalkyl group, where said alkyl group is optionally substituted with one or more groups selected from the group consisting of hydroxyl and alkoxy, a phenyl group optionally substituted with one or more $C_1$-$C_4$ alkoxy groups, or a heteroaryl group; or (2) form, together with the carbon atom which bears them:

a $C_4$-$C_8$ cycloalkyl group, or a 4- to 8-membered saturated heterocyclic group comprising a heteroatom selected from the group consisting of an N, O and S atom, wherein said heterocyclic group is optionally fused with a phenyl group.

6. The compound according to claim 1, wherein $R_3$ is:

a linear or branched $C_1$-$C_7$ alkyl group or a $C_3$-$C_7$ alkyl group in which at least 3 carbon atoms are cyclized, said alkyl group being optionally substituted with one or more groups selected from the group consisting of hydroxyl, alkoxy, —NRR' and haloalkyl, where R and R' are as defined hereinafter;

a —$(CH_2)_n$-heterocyclic group, where n=0, 1, 2 or 3 and where the heterocyclic group comprises between 4 and 8 members and comprises at least one heteroatom selected from the group consisting of an N and O atom, where said heterocyclic group is optionally substituted with an oxo group, or a —$(CH_2)_n$-heteroaryl group, where n=0 or 1 and where the heteroaryl group comprises 5 or 6 members and comprises one or more nitrogen heteroatoms.

7. The compound according to claim 1, wherein $R_4$ is a $C_1$-$C_4$ alkyl group or a $C_1$-$C_4$ alkoxy group.

8. The compound according to claim 1, wherein R and R' are each a linear or branched $C_1$-$C_4$ alkyl group.

9. The compound according to claim 1, selected from the group consisting of:

2-amino-1-ethyl-7-(3-hydroxy-3-methylbut-1-yn-1-yl)-N-methyl-4-oxo-1,4-dihydro-1,8-naphthyridine-3-carboxamide;

(±)-2-amino-1-ethyl-7-[(1-hydroxycyclopentyl)ethynyl]-N-methyl-4-oxo-1,4-dihydro-1,8-naphthyridine-3-carboxamide;

(±)-2-amino-1-ethyl-7-(3-hydroxybut-1-yn-1-yl)-N-methyl-4-oxo-1,4-dihydro-1,8-naphthyridine-3-carboxamide;

(±)-2-amino-1-ethyl-7-(3-hydroxy-3-methylpent-1-yn-1-yl)-N-methyl-4-oxo-1,4-dihydro-1,8-naphthyridine-3-carboxamide;

(±)-2-amino-1-ethyl-7-(3-hydroxy-4-methoxy-3-methylbut-1-yn-1-yl)-N-methyl-4-oxo-1,4-dihydro-1,8-naphthyridine-3-carboxamide;

(±)-2-amino-7-(3-cyclopentyl-3-hydroxyprop-1-yn-1-yl)-1-ethyl-N-methyl-4-oxo-1,4-dihydro-1,8-naphthyridine-3-carboxamide;

(±)-2-amino-7-(3-cyclopropyl-3-hydroxyprop-1-yn-1-yl)-1-ethyl-N-methyl-4-oxo-1,4-dihydro-1,8-naphthyridine-3-carboxamide;

2-amino-1-ethyl-7-[(1-hydroxycyclobutyl)ethynyl]-N-methyl-4-oxo-1,4-dihydro-1,8-naphthyridine-3-carboxamide;

(±)-2-amino-7-(3,4-dihydroxy-3-methylbut-1-yn-1-yl)-1-ethyl-N-methyl-4-oxo-1,4-dihydro-1,8-naphthyridine-3-carboxamide;

2-amino-1-ethyl-7-[3-hydroxy-4-methoxy-3-(methoxymethyl)but-1-yn-1-yl]-N-methyl-4-oxo-1,4-dihydro-1,8-naphthyridine-3-carboxamide;

(±)-2-amino-1-(cyclopropylmethyl)-7-(3-hydroxy-4-methoxy-3-methylbut-1-yn-1-yl)-N-methyl-4-oxo-1,4-dihydro-1,8-naphthyridine-3-carboxamide;

(±)-2-amino-1-ethyl-7-(3-hydroxy-3-phenylbut-1-yn-1-yl)-N-methyl-4-oxo-1,4-dihydro-1,8-naphthyridine-3-carboxamide;

(±)-2-amino-1-ethyl-7-[3-hydroxy-3-(3-thienyl)but-1-yn-1-yl]-N-methyl-4-oxo-1,4-dihydro-1,8-naphthyridine-3-carboxamide;

(±)-2-amino-1-ethyl-7-[3-hydroxy-3-(3-methoxyphenyl)but-1-yn-1-yl]-N-methyl-4-oxo-1,4-dihydro-1,8-naphthyridine-3-carboxamide;

(±)-2-amino-1-ethyl-7-[3-hydroxy-3-(4-methoxyphenyl)but-1-yn-1-yl]-N-methyl-4-oxo-1,4-dihydro-1,8-naphthyridine-3-carboxamide;

(±)-2-amino-7-(3-hydroxy-4-methoxy-3-methylbut-1-yn-1-yl)-1-(3-methoxypropyl)-N-methyl-4-oxo-1,4-dihydro-1,8-naphthyridine-3-carboxamide;

(±)-2-amino-1-cyclopentyl-7-(3-hydroxy-4-methoxy-3-methylbut-1-yn-1-yl)-N-methyl-4-oxo-1,4-dihydro-1,8-naphthyridine-3-carboxamide;

(±)-2-amino-7-(3-hydroxy-4-methoxy-3-methylbut-1-yn-1-yl)-1-isopropyl-N-methyl-4-oxo-1,4-dihydro-1,8-naphthyridine-3-carboxamide;

(±)-2-amino-7-(3-hydroxy-4-methoxy-3-methylbut-1-yn-1-yl)-1-isobutyl-N-methyl-4-oxo-1,4-dihydro-1,8-naphthyridine-3-carboxamide;

2-amino-7-(3-hydroxy-3-methylbut-1-yn-1-yl)-1-(3-methoxypropyl)-N-methyl-4-oxo-1,4-dihydro-1,8-naphthyridine-3-carboxamide;

(±)-2-amino-1-ethyl-7-(3-hydroxy-4-methoxy-3-phenylbut-1-yn-1-yl)-N-methyl-4-oxo-1,4-dihydro-1,8-naphthyridine-3-carboxamide;

(±)-2-amino-1-(tetrahydropyran-4-yl)-7-(3-hydroxy-4-methoxy-3-methylbut-1-yn-1-yl)-N-methyl-4-oxo-1,4-dihydro-1,8-naphthyridine-3-carboxamide;

(±)-2-amino-1-cyclohexyl-7-(3-hydroxy-4-methoxy-3-methylbut-1-yn-1-yl)-N-methyl-4-oxo-1,4-dihydro-1,8-naphthyridine-3-carboxamide;

(±)-2-amino-1-ethyl-7-[3-hydroxy-3-(1,3-thiazol-2-yl)but-1-yn-1-yl]-N-methyl-4-oxo-1,4-dihydro-1,8-naphthyridine-3-carboxamide;

(±)-2-amino-1-ethyl-7-[3-hydroxy-3-(methoxymethyl)pent-1-yn-1-yl]-N-methyl-4-oxo-1,4-dihydro-1,8-naphthyridine-3-carboxamide;

(±)-2-amino-7-(3-hydroxy-4-methoxy-3-methylbut-1-yn-1-yl)-N-methyl-4-oxo-1-[3-(2-oxopyrrolidin-1-yl)propyl]-1,4-dihydro-1,8-naphthyridine-3-carboxamide;

(±)-2-amino-7-(3-hydroxy-4-methoxy-3-methylbut-1-yn-1-yl)-N-methyl-4-oxo-1-propyl-1,4-dihydro-1,8-naphthyridine-3-carboxamide;

(±)-2-amino-7-(3-hydroxy-4-methoxy-3-methylbut-1-yn-1-yl)-N-methyl-4-oxo-1-(2,2,2-trifluoroethyl)-1,4-dihydro-1,8-naphthyridine-3-carboxamide;

(±)-2-amino-7-(3-hydroxy-3-methylbut-1-yn-1-yl)-N-methyl-4-oxo-1-(tetrahydrofuran-2-ylmethyl)-1,4-dihydro-1,8-naphthyridine-3-carboxamide;

(±)-2-amino-7-(3-hydroxy-4-methoxy-3-methylbut-1-yn-1-yl)-N-methyl-4-oxo-1-(pyridin-2-ylmethyl)-1,4-dihydro-1,8-naphthyridine-3-carboxamide;

(±)-2-amino-1-ethyl-7-(3-hydroxy-3-pyrazin-2-ylbut-1-yn-1-yl)-N-methyl-4-oxo-1,4-dihydro-1,8-naphthyridine-3-carboxamide;

(±)-2-amino-7-(3-cyclopropyl-3-hydroxy-4-methoxybut-1-yn-1-yl)-1-ethyl-N-methyl-4-oxo-1,4-dihydro-1,8-naphthyridine-3-carboxamide;

(±)-2-amino-1-ethyl-7-[3-hydroxy-3-(2-thienyl)but-1-yn-1-yl]-N-methyl-4-oxo-1,4-dihydro-1,8-naphthyridine-3-carboxamide;

(±)-2-amino-1-ethyl-7-[3-hydroxy-3-(2-methoxyphenyl)but-1-yn-1-yl]-N-methyl-4-oxo-1,4-dihydro-1,8-naphthyridine-3-carboxamide;

(±)-2-amino-1-cyclopentyl-7-(3,4-dihydroxy-3-methylbut-1-yn-1-yl)-N-methyl-4-oxo-1,4-dihydro-1,8-naphthyridine-3-carboxamide;

(±)-2-amino-7-(4-ethoxy-3-hydroxy-3-methylbut-1-yn-1-yl)-1-ethyl-N-methyl-4-oxo-1,4-dihydro-1,8-naphthyridine-3-carboxamide;

(±)-2-amino-1-(trans-4-hydroxycyclohexyl)-7-(3-hydroxy-4-methoxy-3-methylbut-1-yn-1-yl)-N-methyl-4-oxo-1,4-dihydro-1,8-naphthyridine-3-carboxamide;

(±)-2-amino-7-(3-hydroxy-4-methoxy-3-methylbut-1-yn-1-yl)-N-methyl-1-[3-(methylsulphonyl)propyl]-4-oxo-1,4-dihydro-1,8-naphthyridine-3-carboxamide;

(−)-2-amino-1-(cyclopropylmethyl)-7-(3-hydroxy-4-methoxy-3-methylbut-1-yn-1-yl)-N-methyl-4-oxo-1,4-dihydro-1,8-naphthyridine-3-carboxamide;

(+)-2-amino-1-(cyclopropylmethyl)-7-(3-hydroxy-4-methoxy-3-methylbut-1-yn-1-yl)-N-methyl-4-oxo-1,4-dihydro-1,8-naphthyridine-3-carboxamide;

(+)-2-amino-7-(3,4-dihydroxy-3-methylbut-1-yn-1-yl)-1-ethyl-N-methyl-4-oxo-1,4-dihydro-1,8-naphthyridine-3-carboxamide;

(−)-2-amino-7-(3,4-dihydroxy-3-methylbut-1-yn-1-yl)-1-ethyl-N-methyl-4-oxo-1,4-dihydro-1,8-naphthyridine-3-carboxamide;

(−)-2-amino-1-ethyl-7-(3-hydroxy-3-phenylbut-1-yn-1-yl)-N-methyl-4-oxo-1,4-dihydro-1,8-naphthyridine-3-carboxamide;

(+)-2-amino-1-ethyl-7-(3-hydroxy-3-phenylbut-1-yn-1-yl)-N-methyl-4-oxo-1,4-dihydro-1,8-naphthyridine-3-carboxamide;

(−)-2-amino-7-(3-hydroxy-4-methoxy-3-methylbut-1-yn-1-yl)-1-(3-methoxypropyl)-N-methyl-4-oxo-1,4-dihydro-1,8-naphthyridine-3-carboxamide;

(+)-2-amino-7-(3-hydroxy-4-methoxy-3-methylbut-1-yn-1-yl)-1-(3-methoxypropyl)-N-methyl-4-oxo-1,4-dihydro-1,8-naphthyridine-3-carboxamide;

(−)-2-amino-1-cyclopentyl-7-(3-hydroxy-4-methoxy-3-methylbut-1-yn-1-yl)-N-methyl-4-oxo-1,4-dihydro-1,8-naphthyridine-3-carboxamide;

(+)-2-amino-1-cyclopentyl-7-(3-hydroxy-4-methoxy-3-methylbut-1-yn-1-yl)-N-methyl-4-oxo-1,4-dihydro-1,8-naphthyridine-3-carboxamide;

(−)-2-amino-7-(3-hydroxy-4-methoxy-3-methylbut-1-yn-1-yl)-1-isopropyl-N-methyl-4-oxo-1,4-dihydro-1,8-naphthyridine-3-carboxamide;

(+)-2-amino-7-(3-hydroxy-4-methoxy-3-methylbut-1-yn-1-yl)-1-isopropyl-N-methyl-4-oxo-1,4-dihydro-1,8-naphthyridine-3-carboxamide;

(−)-2-amino-1-cyclohexyl-7-(3-hydroxy-4-methoxy-3-methylbut-1-yn-1-yl)-N-methyl-4-oxo-1,4-dihydro-1,8-naphthyridine-3-carboxamide;

(+)-2-amino-1-cyclohexyl-7-(3-hydroxy-4-methoxy-3-methylbut-1-yn-1-yl)-N-methyl-4-oxo-1,4-dihydro-1,8-naphthyridine-3-carboxamide;

(−)-2-amino-1-ethyl-7-(3-hydroxy-4-methoxy-3-methylbut-1-yn-1-yl)-N-methyl-4-oxo-1,4-dihydro-1,8-naphthyridine-3-carboxamide;

(+)-2-amino-1-ethyl-7-(3-hydroxy-4-methoxy-3-methylbut-1-yn-1-yl)-N-methyl-4-oxo-1,4-dihydro-1,8-naphthyridine-3-carboxamide;

(−)-2-amino-7-(3-hydroxy-4-methoxy-3-methylbut-1-yn-1-yl)-N-methyl-4-oxo-1-propyl-1,4-dihydro-1,8-naphthyridine-3-carboxamide;

(+)-2-amino-7-(3-hydroxy-4-methoxy-3-methylbut-1-yn-1-yl)-N-methyl-4-oxo-1-propyl-1,4-dihydro-1,8-naphthyridine-3-carboxamide;

(−)-2-amino-7-(3-hydroxy-4-methoxy-3-methylbut-1-yn-1-yl)-N-methyl-4-oxo-1-(2,2,2-trifluoroethyl)-1,4-dihydro-1,8-naphthyridine-3-carboxamide;

(+)-2-amino-7-(3-hydroxy-4-methoxy-3-methylbut-1-yn-1-yl)-N-methyl-4-oxo-1-(2,2,2-trifluoroethyl)-1,4-dihydro-1,8-naphthyridine-3-carboxamide;

(+)-2-amino-1-ethyl-7-[3-hydroxy-3-(methoxymethyl)pent-1-yn-1-yl]-N-methyl-4-oxo-1,4-dihydro-1,8-naphthyridine-3-carboxamide;

(−)-2-amino-1-ethyl-7-[3-hydroxy-3-(methoxymethyl)pent-1-yn-1-yl]-N-methyl-4-oxo-1,4-dihydro-1,8-naphthyridine-3-carboxamide;

(+)-2-amino-1-ethyl-7-[3-hydroxy-3-(3-thienyl)but-1-yn-1-yl]-N-methyl-4-oxo-1,4-dihydro-1,8-naphthyridine-3-carboxamide; and (−)-2-amino-1-ethyl-7-[3-hydroxy-3-(3-thienyl)but-1-yn-1-yl]-N-methyl-4-oxo-1,4-dihydro-1,8-naphthyridine-3-carboxamide;

or an acid addition salt thereof.

10. A process for preparing the compound according to claim 1, comprising reacting a compound of formula (VII):

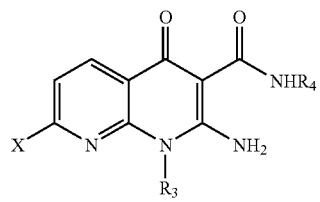

(VII)

wherein X is a halogen atom and $R_3$ and $R_4$ are as defined in claim 1, with a compound of formula (VIII):

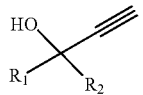

wherein $R_1$ and $R_2$ are as defined in claim 1.

11. A pharmaceutical composition comprising the compound according to claim 1, or a pharmaceutically acceptable salt, or an enantiomer or a diastereoisomer, or a mixture thereof, and also at least one pharmaceutically acceptable excipient.

12. A pharmaceutical composition comprising the compound according to claim 9, or a pharmaceutically acceptable salt thereof, and also at least one pharmaceutically acceptable excipient.

* * * * *